US012732950B1

(12) United States Patent
Tisdale

(10) Patent No.: US 12,732,950 B1

(45) Date of Patent: Sep. 8, 2026

(54) DISCREET AND WEARABLE TRACKING DEVICES

(71) Applicant: Joy D. Tisdale, Atlanta, GA (US)

(72) Inventor: Joy D. Tisdale, Atlanta, GA (US)

(73) Assignee: Joy D. Tisdale, Atlanta, GA (US)

( * ) Notice: Subject to any disclaimer, the term of this patent is extended or adjusted under 35 U.S.C. 154(b) by 310 days.

(21) Appl. No.: 18/408,843

(22) Filed: Jan. 10, 2024

(51) Int. Cl.

*H04W 64/00* (2009.01)

*G16H 10/60* (2018.01)

*H04W 4/021* (2018.01)

(52) U.S. Cl.

CPC .......... *H04W 64/003* (2013.01); *G16H 10/60* (2018.01); *H04W 4/021* (2013.01)

(58) Field of Classification Search

CPC ..... H04W 64/003; H04W 4/021; G16H 10/60

See application file for complete search history.

(56) References Cited

U.S. PATENT DOCUMENTS

| | | | | |
|---|---|---|---|---|
| 2017/0002586 | A1* | 1/2017 | Lee | E05B 39/00 |
| 2021/0274315 | A1* | 9/2021 | Daoura | H04W 4/38 |
| 2021/0401331 | A1* | 12/2021 | Flores | A61B 5/024 |
| 2022/0287112 | A1* | 9/2022 | Ming | G01K 1/14 |
| 2024/0073219 | A1* | 2/2024 | Maizels | G10L 13/00 |

* cited by examiner

*Primary Examiner* — Fred A Casca

(74) *Attorney, Agent, or Firm* — Nelson Mullins Riley & Scarborough LLP

(57) ABSTRACT

A system for tracking a tracking device is provided. The tracking device comprises a wearable component that is a bracelet, earring, necklace, ring, band aid, diaper, shoe, hat, pacifier, hair tie, glasses, and/or clothing. The wearable component has an attachment feature configured to enable attachment of the wearable component to a body of a person, hair, clothing, and/or an accessory. The tracking device comprises a tracking unit comprising a location sensor. The system comprises an additional device, processor(s), and memory having a computer program code stored thereon. The computer program code is configured to store data and, when executed, cause the processor(s) to receive a geographical location of the tracking device based on the location sensor's satellite global positioning system coordinates, identify the additional device, and cause an indication of the tracking device's geographical location to be sent to the additional device.

19 Claims, 21 Drawing Sheets

Receive Geographical Location of Tracking Device
1002
Identify an Additional Device
1004
Cause an Indication of the Geographical Location of the Tracking Device to be Sent to the Additional Device
1006

1000

1100

START
Receive Geographical Location of Tracking Device
1102
Is Tracking Device Outside of Specified Area?
1104
NO
YES
Identify a Additional Device
1106
Cause an Indication of the Geographical Location of the Tracking Device to be Sent to the Additional Device
1108

Receive Body Temperature Data
1202
Cause the Temperature Data to be Stored in Memory
1204
Cause an Indication of the Body Temperature to be Sent to the Additional Device
1206

1200

FIG. 13
1300
Receive Health Data
1302
Cause the Health Data to be Stored in Memory
1304
Cause the Health Data to be Sent to the Additional Device
1306

START
Is Device is in Close Proximity to a Lock? 1402
NO
YES
Cause a Signal to be Sent or Received Upon the Device Coming in Close Proximity to a Lock 1404
Cause the Lock to Change to Either an Opened State or a Locked State 1406

1400

START
Is Device is in
Close Proximity to Payment Device?
1502
NO
YES
Cause a Signal to be Sent or Received Upon the Device
Coming in Close Proximity to the Payment Device
1504
Cause an Electronic Payment to be Made
1506

1500

DISCREET AND WEARABLE TRACKING DEVICES

TECHNICAL FIELD

Embodiments relate generally to wearable tracking devices that are discreet.

BACKGROUND OF THE INVENTION

Currently, the rate of childhood kidnapping, sex trafficking, and missing persons is alarmingly high. The types of equipment that are currently available to help stop these tragedies from happening have issues that limit their effectiveness. For example, location tracking of children or loved ones may be completed using a smartphones, a tablet, a smartwatch, etc. Yet, if a kidnapper is near a child, one of the first things that the kidnapper will do is take these smartphones, tablets, smartwatches, etc. and leave them at a certain location to prevent the child from being tracked. Also, such devices can be too complicated for all children and/or too expensive.

SUMMARY OF THE INVENTION

The tracking devices provided herein may be provided in unique wearable components such as band-aids, diapers, rings, bracelets, necklaces, glasses or other wearable components. Wearable components of these forms typically do not contain tracking devices therein and do not contain any electronic devices therein, so they provide a discrete solution and kidnappers or others presenting danger to the user may not think to remove the wearable components, increasing the likelihood that the user can be tracked down. Thus, the discreet nature of tracking devices may be a significant advantage over any existing approaches for tracking users. Additionally, the discreet nature of the device may also be beneficial to allow a parent to track the location of their child without the child knowing.

In some embodiments, tracking devices may be utilized to notify police, medical workers, and/or other local authorities that the user is potentially in danger. The tracking devices may notify these authorities, for example, if the tracking device exits a specified geographical area that the tracking device is permitted to roam within, if a button on the tracking device is pressed, or if other information indicates that the user is potentially in danger. This may provide parents and other loved ones with peace of mind that authorities will quickly respond to any potential danger.

Additionally, the tracking devices may have their locations tracked through the use of satellites, and the satellite communication may be used to contact local authorities or parents, friends, loved ones, etc. in a reliable manner. By using satellite systems to track the location, the use of cellular networks may be avoided. Thus, location tracking may be made more reliable as the location may be determined even when the tracking device is located in an area having limited cellular network coverage.

In an example embodiment, a system for tracking a tracking device is provided. The system comprises the tracking device. The tracking device comprises a wearable component that is at least one of a bracelet, an earring, a necklace, a ring, a band aid, a diaper, a shoe, a hat, a pacifier, a hair tie, glasses, or clothing. The wearable component has an attachment feature configured to enable attachment of the wearable component to at least one of a body of a person, hair, clothing, or an accessory. The tracking device also comprises a tracking unit comprising a location sensor. The system also comprises an additional device, at least one processor, at least one memory having a computer program code stored thereon and configured to store data. The computer program code is configured to, when executed by the processor(s), cause the processor(s) to receive a geographical location of the tracking device based on satellite global positioning system coordinates for the location sensor, to identify the additional device, and to cause an indication of the geographical location of the tracking device to be sent to the additional device.

In some embodiments, the additional device may be at least one of a cell phone, a pager, a display, a computer, a tablet, or a server. In some embodiments, the indication of the geographical location of the tracking device may be at least one of a map that illustrates a position of the tracking device, a longitude and latitude of the tracking device, or a city, town, neighborhood, or street that the tracking device is positioned in or proximate to.

In some embodiments, the computer program code, when executed by the processor(s), may cause the processor(s) to determine whether the tracking device is outside of a specified geographical area. Additionally, in some embodiments, the indication of the geographical location of the tracking device may be a notification that the tracking device is outside of the specified geographical area or a notification to police.

In some embodiments, the tracking device may further comprise a temperature sensor configured to receive body temperature data regarding a body temperature of a user wearing the tracking device. Additionally, the computer program code, when executed by the processor(s), may cause the processor(s) to cause an indication of the body temperature to be sent to the additional device. The indication of the body temperature may be at least one of a notification containing the body temperature data, a notification indicating that the body temperature of the user wearing the device falls outside of a normal range, a notification stating a potential illness, or a duration of time that the body temperature of the user wearing the device has fallen outside of the normal range.

In some embodiments, the computer program code, when executed by the processor(s), may cause the processor(s) to receive health data regarding at least one health aspect of a user wearing the tracking device, with the health aspect(s) being at least one of a heart rate, a body temperature, or a breathing rate. The computer program code, when executed by the processor(s), may also cause the health data to be stored in the memory device(s) or sent to the additional device. In some embodiments, the computer program code, when executed by the processor(s), may cause the processor(s) to send or receive a signal upon the tracking device coming in close proximity to a payment device and to cause an electronic payment to be made upon the payment signal being sent or received.

In some embodiments, the computer program code, when executed by the processor(s), may cause the processor(s) to send or receive a signal upon the tracking device coming in close proximity to a lock and may also cause a lock to be opened upon the signal being sent or received. In some embodiments, at least a portion of the tracking device may be waterproof. In some embodiments, the processor(s) and the memory device(s) may be positioned in the tracking unit, and the tracking unit may be removably attachable to the wearable component. In some embodiments, the tracking device may comprise a button, and the computer program code, when executed by the processor(s), may cause the processor(s) to receive an indication that the button has been pressed and, upon receiving the indication that the button has been pressed, cause an alert to be sent to the additional device.

In another example embodiment, a tracking device is provided. The tracking device comprises a wearable component that is at least one of a bracelet, an earring, a necklace, a ring, a band aid, a diaper, a shoe, glasses, or clothing. The wearable component has an attachment feature configured to enable attachment of the wearable component to at least one of a body of a person, hair, clothing, or an accessory. The tracking device also comprises a tracking unit comprising a location sensor, at least one processor configured to control operation of the tracking device, and at least one memory having a computer program code stored thereon and configured to store data. The computer program code is configured to, when executed by the processor(s), cause the processor(s) to receive a geographical location of the tracking device based on satellite global positioning system coordinates for the location sensor, to identify the additional device, and to cause an indication of the geographical location of the tracking device to be sent to the additional device.

In some embodiments, the additional device may be at least one of a cell phone, a pager, a display, a computer, a tablet, or a server. Additionally, in some embodiments, the indication of the geographical location of the tracking device may be at least one of a map that illustrates a position of the tracking device, a longitude and latitude of the tracking device, or a city, town, neighborhood, or street that the tracking device is positioned in or proximate to. Furthermore, in some embodiments, the computer program code, when executed by the processor(s), may cause the processor(s) to determine whether the tracking device is outside of a specified geographical area, and the indication of the geographical location of the tracking device may be a notification that the tracking device is outside of the specified geographical area or a notification to police.

In some embodiments, the wearable component may comprise a first portion and a second portion, the processor(s) and the memory device(s) may be positioned in the second portion, and the second portion may be removably attachable to the first portion. In some embodiments, the wearable component may comprise a button. The computer program code, when executed by the processor(s), may cause the processor(s) to receive an indication that the button has been pressed, and may, upon receiving the indication that the button has been pressed, cause an additional device to receive an alert.

In another example embodiment, a method for operating a tracking device is provided. The method comprises receiving a geographical location of the tracking device based on satellite global positioning system coordinates, identifying an additional device, and sending an indication of the geographical location of the tracking device to the additional device. The tracking device comprises a wearable component having an attachment feature configured to enable attachment of the wearable component to at least one of a body of a person, hair, clothing, or an accessory. Additionally, in some embodiments, the method also comprises determining whether the tracking device is outside of a specified geographical area.

BRIEF DESCRIPTION OF THE DRAWINGS

Reference will now be made to the accompanying drawings, which are not necessarily drawn to scale, and wherein.

DETAILED DESCRIPTION

Figure 1:
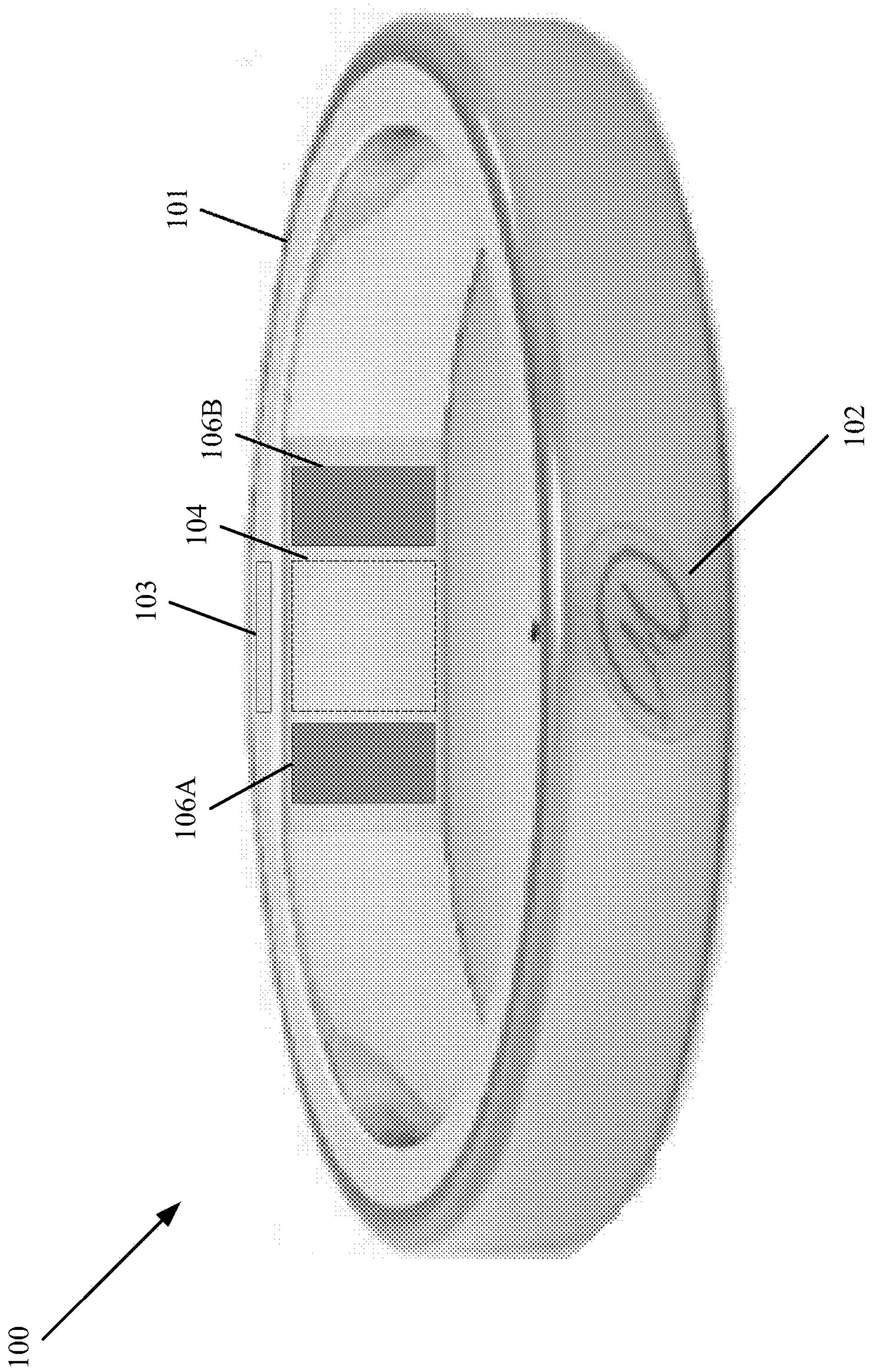
FIG. 1 is a perspective, schematic-type view illustrating an example tracking device comprising a wearable component in the form of a ring, in accordance with some embodiments discussed herein.

Example embodiments now will be described more fully hereinafter with reference to the accompanying drawings, in which some, but not all embodiments are shown. Like reference numerals generally refer to like elements throughout. For example, reference numbers 100, 200, 300, 400, 500, and 600 are each associated with tracking devices. Additionally, any connections or attachments may be direct or indirect connections or attachments unless specifically noted otherwise.

FIG. 1 is a schematic view illustrating an example tracking device 100. The tracking device 100 comprises a wearable component 101 in the form of a ring and a tracking unit 104. The tracking unit 104 may comprise one or more processors and one or more memory devices. In some embodiments, the tracking unit 104 may be removably attachable to the remainder of the wearable component 101. The ability to easily insert the tracking unit or remove the tracking unit may be beneficial for maintenance and for other reasons. In the tracking device 100, the tracking unit 104 may be inserted or removed by removing the removably attachable wall section 103, which may be attached via fasteners or through other approaches.

The tracking device 100 comprises a button 102. Upon the button 102 being pressed, one or more processors in the tracking device 100 or at another location may receive an indication that the button 102 has been pressed and then cause an alert or other information to be sent to another device. For example, upon the button 102 being pressed by a user, an alert or other information may be presented on the device of a parent of the user, a relative of the user, a friend of the user, a coworker of the user, government authorities, police, or medical support. However, an alert or other information may be sent to a wide variety of recipients, and signals may be sent to multiple recipients (e.g., various police officers in close proximity). When the button 102 is pressed (e.g., once, for a certain period of time, and/or according to a certain pattern (e.g., SOS pattern, two taps, among others)), a distress signal may be sent out to indicate that the user is in danger. In some embodiments, upon the button being pressed, the button 102 may be illuminated. The light may signify that the authorities and/or others have been notified and that help is on the way, and the light may be a faint light in some embodiments to prevent the user from being easily found by a potential kidnapper or another attacker. However, in other embodiments, the light may be brighter to allow the user to be more easily found by authorities or others.

In some embodiments, the button 102 must be pressed and held for a certain duration of time (e.g., about three seconds) before any alerts are sent or before any light is generated at the tracking device, and this may be beneficial to prevent alerts from being sent or from causing the light to be generated when the user inadvertently presses down on the button 102. The light may be turned off after a certain duration of time, once the authorities or another individual comes in close proximity to the device or once the authorities or another individual comes to turn the light off (e.g., using a pendant or some other device to send a signal to turn the light off). In some embodiments, the location of the tracking device 100 may only be tracked after the button 102 has been pressed to activate location tracking, but the location of the tracking device 100 may be tracked at all times in other embodiments.

The tracking device 100 may also include sensors 106A, 106B. The sensors 106A, 106B may be utilized to obtain various types of data. For example, one or both of the sensors 106A, 106B may be used to obtain health data regarding a health aspect of the user wearing the tracking device. This health aspect may be the heart rate of the user, the body temperature of the user, the breathing rate of the user, or other types of data. Once the health data is obtained using the sensors 106A, 106B, the health data may be stored in memory at the tracking unit 104 or at another location, or the health data may be sent to another device so that the health data may be displayed. For example, the health data may be sent to the smart phone, tablet, computer, etc. of the user, a parent of the user, etc.

Tracking device 100 may also be configured to identify, track, and store certain biometric information for users and/or others. For example, a user's biometric information may be obtained and stored so that the user can be identified before allowing access to personal health information or other information. In some embodiments, tracking devices 100 may identify the particular user currently using the tracking device 100 based on biometric information, and this may enable more accurate data to be maintained over time. Additionally or alternatively, biometric information for other authorized people such as parents, other loved ones, friends, etc. may also be stored so that these authorized people are enabled to obtain access (but only after a match with their biometric information).

The tracking unit 104 being concealed within the wearable component 101 may be beneficial if the user is in danger because those imposing the danger may be unaware that the wearable component 101 comprises any tracking unit 104. Additionally, this discreet nature of the tracking unit 104 may be beneficial to allow a parent to track a child without the child knowing that the tracking unit 104 is present in the wearable component 101.

Figure 2:
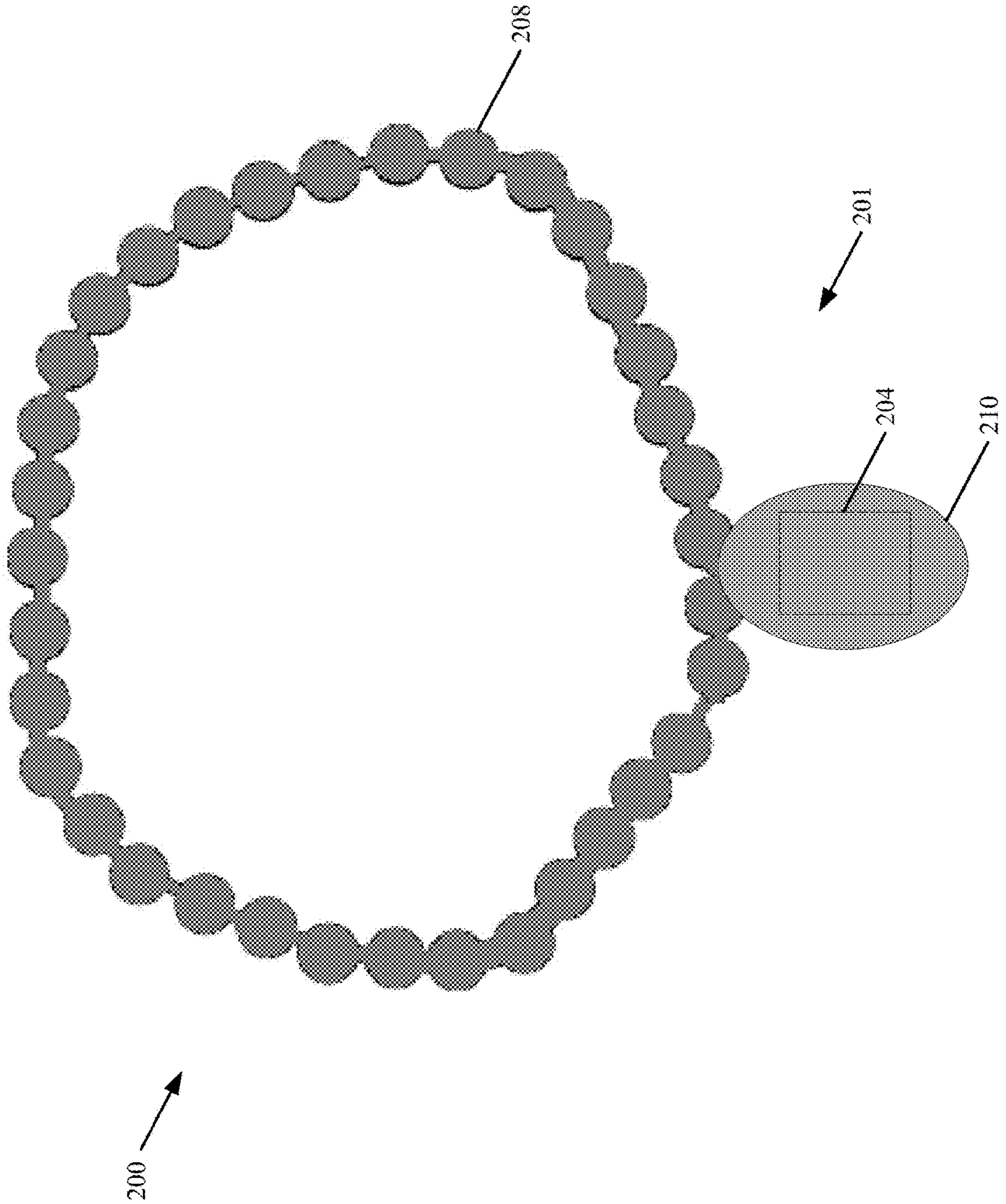
FIG. 2 is a schematic view illustrating an example tracking device comprising a wearable component in the form of a necklace, in accordance with some embodiments discussed herein.

In FIG. 2, the tracking device 200 comprises a wearable component 201 in the form of a necklace, with the wearable component 201 comprising a chain portion 208 and an ornamental portion 210. The tracking device 200 also comprises a tracking unit 204. This tracking unit 204 may be similar to the other tracking units described herein. The tracking unit 204 is positioned in the ornamental portion 210 in the tracking device 200 of FIG. 2, but the tracking unit 204 may be positioned in other locations within the wearable component 201 in other embodiments.

In some embodiments, a button may be provided on the wearable component 201 such as on the chain portion 208 or on the ornamental portion 210, and the button may function similarly to the button 102 of FIG. 1. However, the button may be omitted in other embodiments. The tracking unit 204 being concealed within the wearable component 201 may be beneficial if the user is in danger because those imposing the danger may be unaware that the wearable component 201 comprises any tracking unit 204. Additionally, this discreet nature of the tracking unit 204 may be beneficial to allow a parent to track a child without the child knowing that the tracking unit 204 is present in the wearable component 201.

Figure 3A:
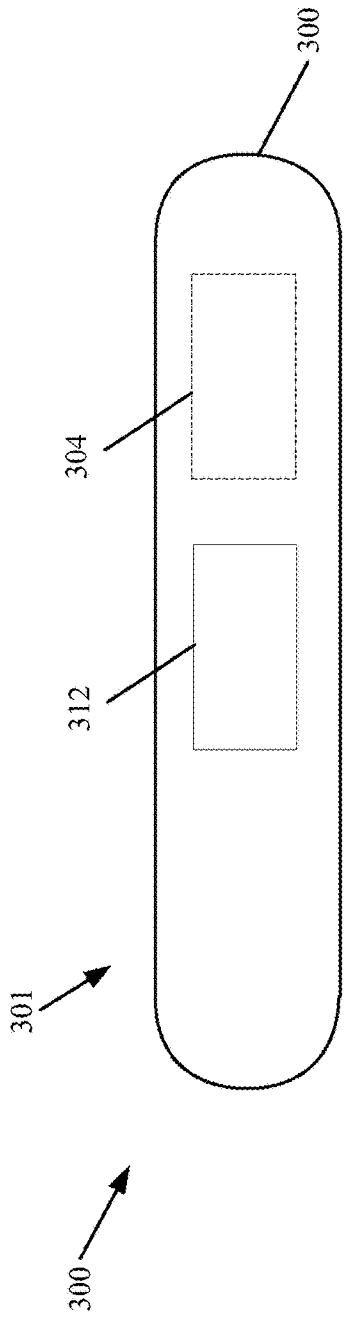
FIG. 3A is a bottom, schematic view illustrating an example tracking device comprising a wearable component in the form of a band-aid, in accordance with some embodiments discussed herein.
Figure 3B:
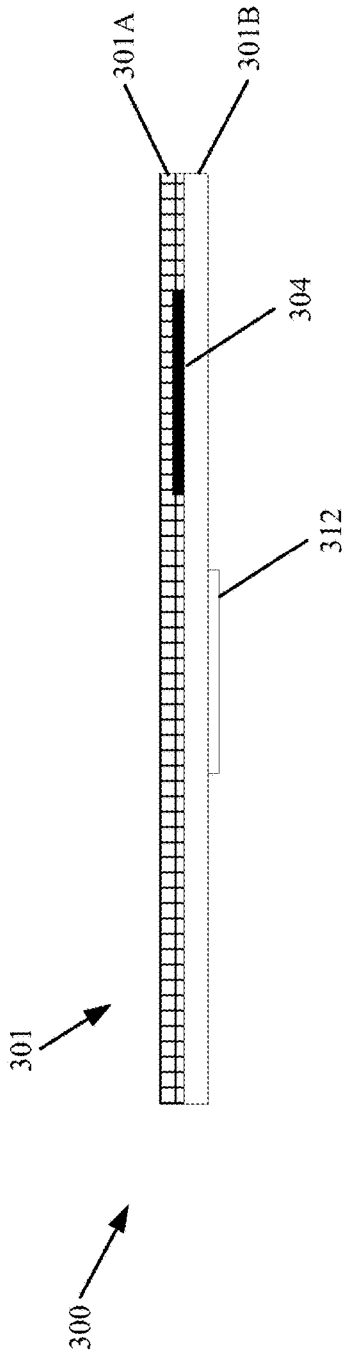
FIG. 3B is a side, schematic view illustrating an example tracking device comprising a wearable component in the form of a band-aid, in accordance with some embodiments discussed herein.

FIGS. 3A and 3B illustrate an example tracking device 300 comprising a wearable component 301 in the form of a band-aid, with FIG. 3A being a bottom, schematic view and with FIG. 3B being a cross-sectional, schematic view. The wearable component 301 comprises a first portion 301A, a second portion 301B, and a cloth portion 312. The tracking device 300 may be positioned at a cut or another wound, with the cloth portion 312 being positioned proximate to the cut or the wound.

The tracking device 300 also comprises a tracking unit 304. This tracking unit 304 may be similar to the other tracking units described herein. The tracking unit 304 is positioned between the first portion 301A and the second portion 301B. In some embodiments, the first portion 301A and the second portion 301B may be removably attachable to each other so that the tracking device 300 may be easily inserted into or removed from the wearable component 301. This may be beneficial to allow maintenance/replacement to occur. In some embodiments, the tracking unit 304 may be embedded in the wearable component 301 during manufacturing, the first portion 301A and the second portion 301B may not be removably attachable to each other, and the wearable component 301 may be used repeatedly. The tracking unit 304 being concealed within the wearable component 301 may be beneficial if the user is in danger because those imposing the danger may be unaware that the wearable component 301 comprises any tracking unit 304. Additionally, the discreet nature of the tracking unit 304 may be beneficial to allow a parent to track a child without the child knowing that the tracking unit 304 is present in the wearable component 301.

In other embodiments, tracking devices may comprise wearable components in the form of diapers. For example, the tracking device 400 of FIG. 4 comprises a wearable component 401 in the form of a diaper, and the tracking device 500 of FIG. 5 comprises a wearable component 501 in the form of a diaper. The wearable component defines an opening 414A, an opening 414B, a front portion (not shown), and a back portion 416.

Figure 4:
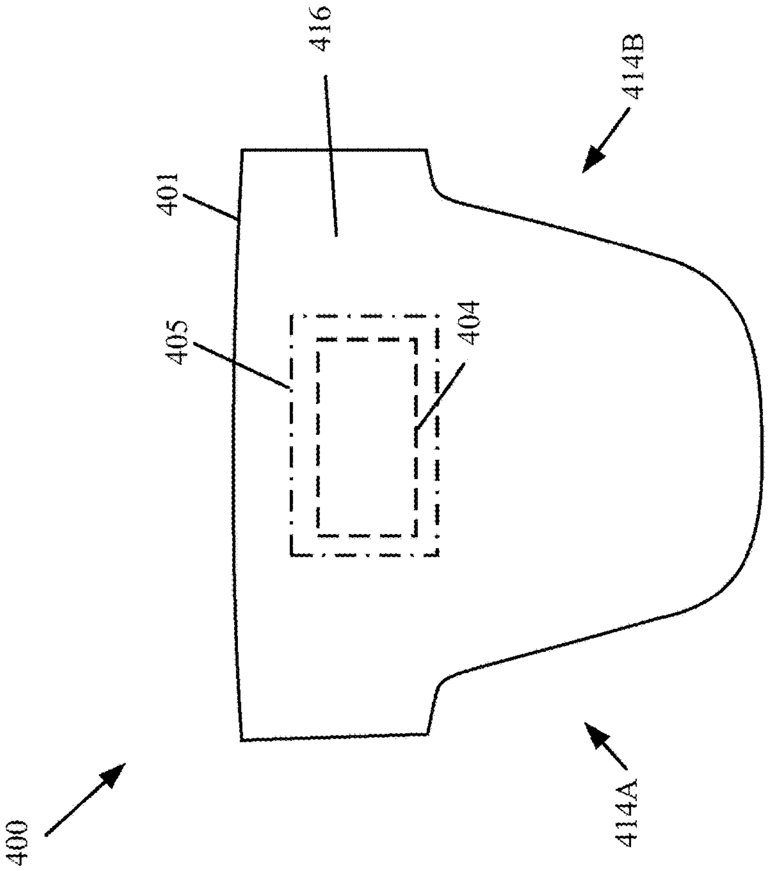
FIGS. 4 and 5 are schematic views illustrating example tracking devices comprising a wearable component in the form of diapers, in accordance with some embodiments discussed herein.

Looking first at FIG. 4, the wearable component 401 defines an attachment slot 405 where the tracking unit 404 may be received. This tracking unit 404 may be similar to the other tracking units described herein. The attachment slot 405 may be positioned at the back portion 416 of the wearable component 401 so that the wearable component 401 may remain comfortable even with the tracking unit 404 positioned therein, but the attachment slot 405 may be positioned elsewhere on the wearable component 401.

Figure 5:
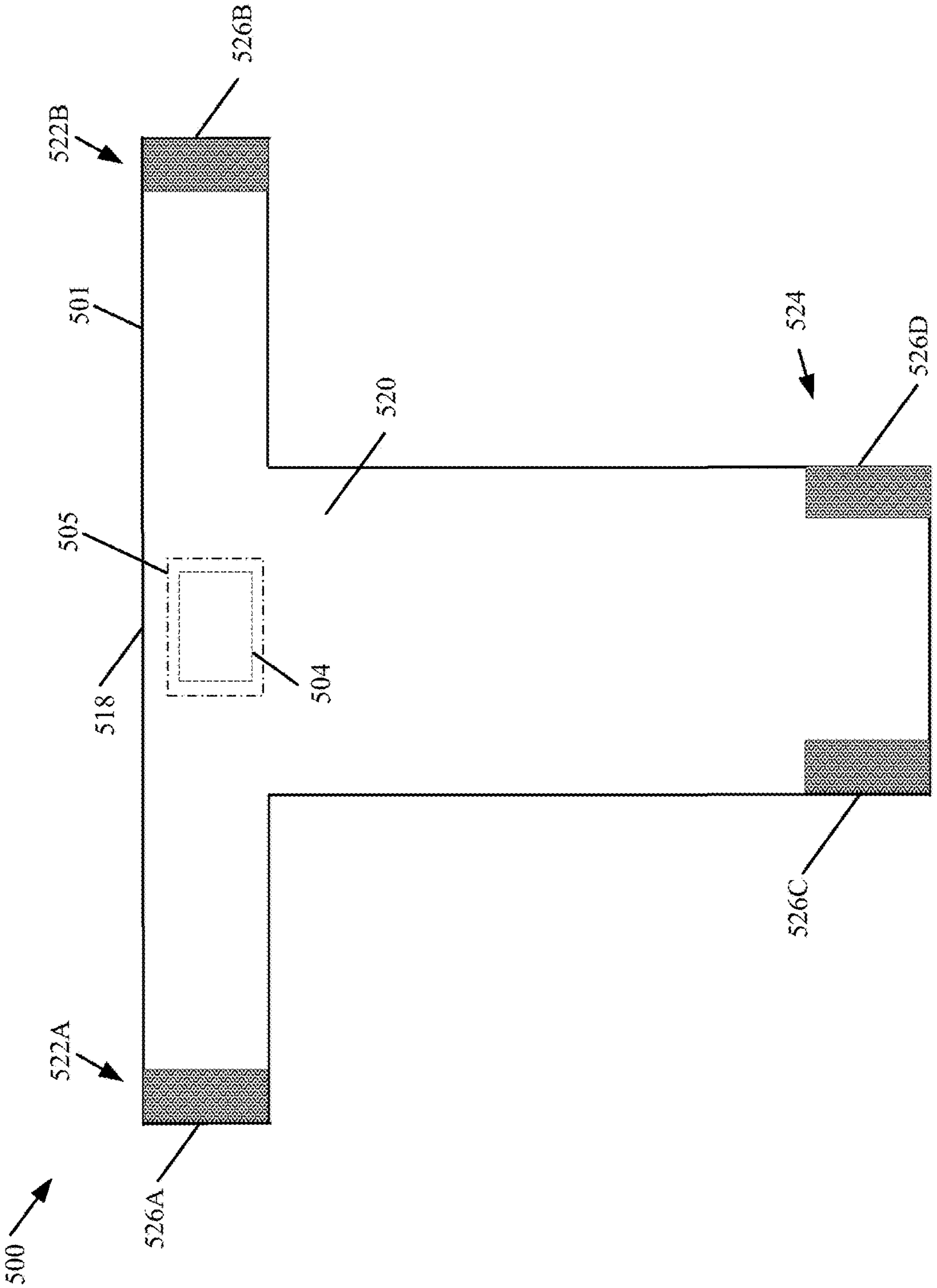

In FIG. 5, the wearable component 501 defines an attachment slot 505 where the tracking unit 504 may be received. This tracking unit 504 may be similar to the other tracking units described herein. The attachment slot 505 may be positioned at the back portion 516 of the wearable component 501 so that the wearable component 501 may remain comfortable even when the tracking unit 504 is positioned therein, but the attachment slot 505 may be positioned elsewhere on the wearable component 501. In some embodiments, additional material or a different type of material may be provided in the wearable components 401, 501 at positions proximate to the attachment slots 405, 505 to improve the comfort of the wearable component 401, 501.

In the wearable component 501 illustrated in FIG. 5, the wearable component 501 is not assembled. The wearable component 501 comprises a first portion 520. The first portion 520 is integrally attached to a second portion 518, and the first portion 520 extends from the area where it is attached to the second portion 518 all the way to the end portion 524. Attachment portions 526C, 526D are positioned at opposing sides of the end portion 524. The wearable component 501 also comprises a second portion 518 extending between a first side 522A and a second side 522B. The first portion 520 is integrally attached to the second portion 518 at a location around a midpoint between the first side 522A and the second side 522B. An attachment portion 526A is positioned at the first side 522A of the second portion 518 and an attachment portion 526B is positioned at the second side 522B of the second portion 518. To assemble the wearable component 501, the first portion 520 may be folded so that the end portion 524 is rotated upwardly towards the second portion 518, and then the attachment portion 526A may be attached to the attachment portion 526C and attachment portion 526B may be attached to the attachment portion 526D.

The tracking unit 404, 504 being concealed within the wearable components 401, 501 may be beneficial if the user is in danger because those imposing the danger may be unaware that the wearable component 401, 501 comprises any tracking unit 404, 504. Additionally, this discreet nature of the tracking unit 404, 504 may be beneficial to allow a parent to track a child without the child knowing that the tracking unit 404 or the tracking unit 504 is present in the respective wearable component.

Figure 6A:
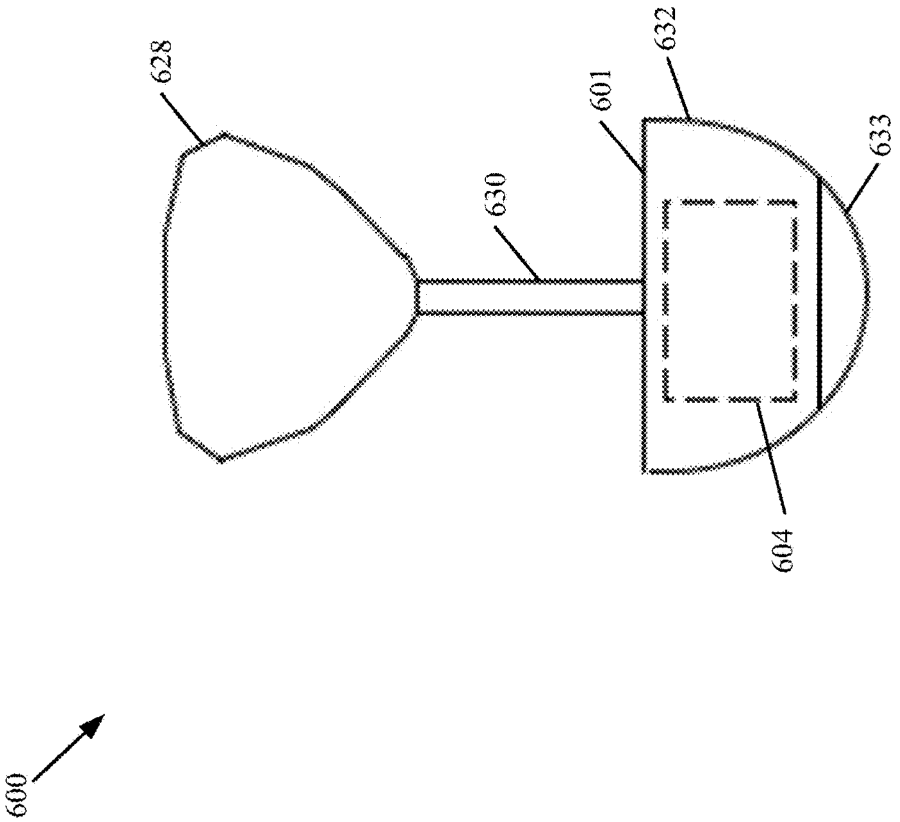
FIG. 6A is a schematic view illustrating an example tracking device comprising a wearable component in the form of an earring, in accordance with some embodiments discussed herein.

In FIG. 6A, the tracking device 600 comprises a wearable component 601 in the form of an earring. The wearable component 601 comprises a head 628, which may be ornamental and may take on a variety of forms. The wearable component 601 also comprises a stem 630 and a base 632, with the stem 630 connecting the head 628 to the base 632. The base 632 may be removably attachable to the stem 630 to allow the earrings to be easily deployed or removed. Additionally, the base 632 also comprises a cover 633, and the cover 633 may be removably attachable to the remainder of the base 632. The cover 633 may be attached using a helical screw engagement between the remainder of the base 632 and the cover 633, but the cover 633 may be attached to the remainder of the base 632 in other ways such as using a hinge, using other fasteners, etc. The cover 633 may be moved to allow access into the base 632, which may enable the tracking unit 604 to be easily inserted into or removed from the base 632. However, in other embodiments, the tracking unit 604 may be positioned at other locations of the wearable component 601 such as in the head 628. This tracking unit 604 may be similar to the other tracking units described herein.

The tracking unit 604 being concealed within the wearable components 601 may be beneficial if the user is in danger because those imposing the danger may be unaware that the wearable component 601 comprises any tracking unit 604. Additionally, the discreet nature of the tracking unit 604 may be beneficial to allow a parent to track a child without the child knowing that the tracking unit 604 is present in the wearable component 601.

The example tracking devices of FIGS. 1-5 and 6A may be waterproof in some embodiments to prevent exposure of the tracking unit within the tracking devices to any water. For example, the tracking devices may have at least an IP65 ingress protection rating to prevent exposure of inner contents of the tracking devices from water, moisture, dirt, and/or other materials.

In some embodiments, the tracking devices of FIGS. 1-5 and 6A may be chargeable using a charging hub so that the tracking device continues to maintain a sufficient amount of power. For example, FIG. 6B illustrates tracking devices 600A, 600B with wearable components in the form of earrings, with these tracking devices 600A, 600B each being similar to the tracking device 600 of FIG. 6A.

Figure 6C:
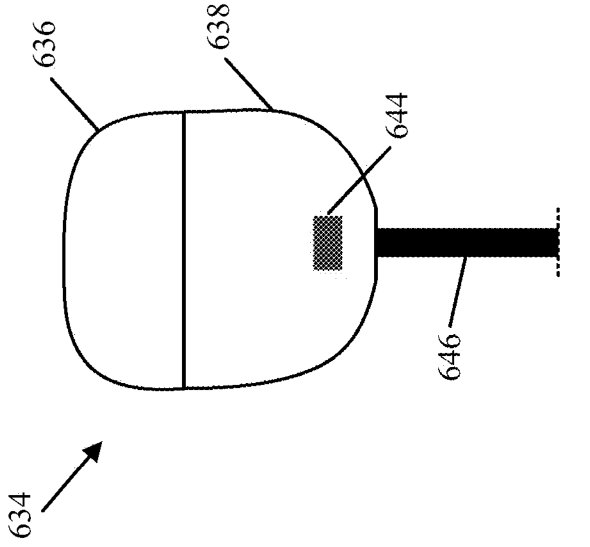
FIG. 6C is a schematic, front view illustrating the charging hub of FIG. 6B, with the charging hub being in a closed state with tracking devices positioned therein, in accordance with some embodiments discussed herein.
Figure 6B:
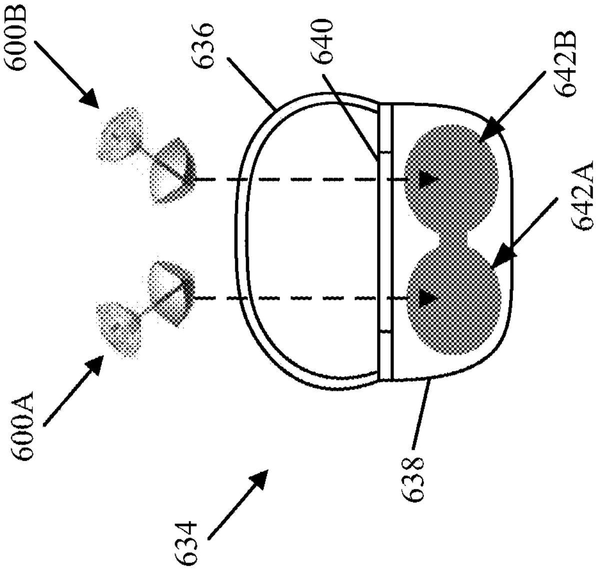
FIG. 6B is a schematic, top view illustrating tracking devices similar to the tracking device of FIG. 6A being inserted into a charging hub for charging, with the charging hub being in an open state, in accordance with some embodiments discussed herein.

In FIG. 6B, the tracking devices 600A, 600B are being inserted into a charging hub 634 for charging, with the charging hub 634 being in an open state. The charging hub 634 comprises a top portion 636 and a base portion 638, with the top portion 636 being pivotably attached to the base portion 638 via a hinge 640. However, the top portion 636 and the base portion 638 may be attached to each other in other ways. When the charging hub 634 is in an opened state as illustrated in FIG. 6B, the tracking devices 600A, 600B may be inserted into slots 642A, 642B respectively so that the tracking devices 600A, 600B may be charged.

In FIG. 6C, the charging hub 634 is illustrated in a closed state. The top portion 636 may be rounded in shape to provide sufficient clearance to allow the top portion 636 to be closed when the tracking devices 600A, 600B are received in the charging hub 634. The charging hub 634 may also be configured to be attached to a charging cable 646 so that power may be provided to the charging hub 634. In some embodiments, the charging hub 634 may be configured to receive power via the charging cable 646 even when the tracking devices 600A, 600B are not positioned in the charging hub 634, and the charging hub 634 may store this energy for later use. Additionally, the charging hub 634 may be configured to charge the tracking devices 600A, 600B even when no charging cable 646 is attached to the charging hub 634, with stored energy being provided to the tracking devices 600A, 600B.

In FIG. 6C, the charging hub 634 is illustrated with a light 644. The light 644 may be configured to be illuminated when the tracking devices 600A, 600B are being charged within the charging hub 634. In some embodiments, the light 644 may be configured to be illuminated in different colors to convey different states for the charging hub 634. For example, the light 644 may be illuminated in a first color (e.g., green) when tracking devices 600A, 600B are positioned in the charging hub 634 and when a charging cable 646 is attached to the charging hub 634, the light 644 may be illuminated in a second color (e.g., blue) when tracking devices 600A, 600B are positioned in the charging hub 634 and when no charging cable 646 is attached to the charging hub 634, the light 644 may be illuminated in a third color (e.g., red) when tracking devices 600A, 600B are not positioned in the charging hub 634 and when the charging cable 646 is attached to the charging hub 634, and the light 644 may not be illuminated at all when the tracking devices 600A, 600B are not positioned in the charging hub 634 and when the charging cable 646 is not attached to the charging hub 634.

Figure 7A:
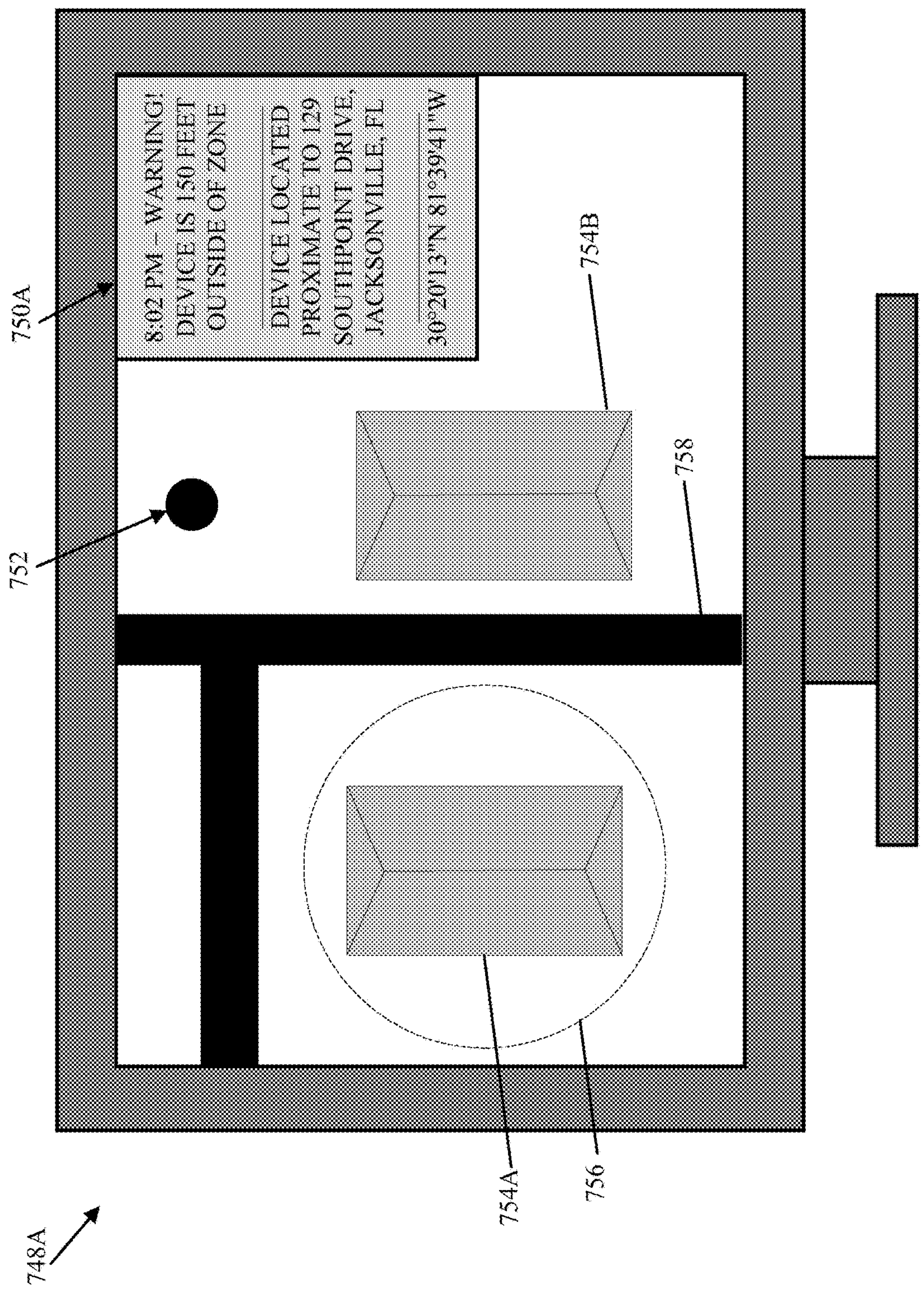
FIG. 7A is a schematic view illustrating an example of an additional device in the form of a display, with the additional device presenting a notification that the tracking device is outside of the specified geographical area, in accordance with some embodiments discussed herein.

In various embodiments contemplated herein, tracking devices may be in communication with one or more additional devices so that information about the tracking devices may be presented to the user or to another user such as a parent. In FIG. 7A, the illustrated device 748A is a display such as a liquid crystal display (LCD), with the device 748A presenting a notification that the tracking device is outside of the specified geographical area. In the device 748A, a screen is presented with a map being shown on the screen. The map includes a tracking device location indication 752 to indicate the location of the tracking device, and the map also illustrates the tracking device location indication 752 relative to the surrounding environment. For example, the map illustrates a first house representation 754A, a second house representation 754B, and representations of roads 758. Thus, the map provides context that is helpful to locate the tracking device.

Additionally, the settings may be configured such that the tracking device is permitted to roam in a specified geographical area, with warnings being generated when the tracking device ventures beyond the specified geographical area. In FIG. 7A, the map illustrates a representation of the specified geographical area 756 proximate to the first house representation 754A, with the tracking device location indication 752 being outside of this area. While the specified geographical area 756 is circular in shape in FIG. 7A, the area may possess other shapes in other embodiments and/or the area may be adjusted by the user, a parent, or by another person. The tracking device location indication 752 may be updated in various frequencies. For example, the tracking device location indication 752 may be updated about once every two seconds, but the frequency may be different in other embodiments.

The device 748A also illustrates an indication 750A in the form of a notification that provides further information. The indication 750A states "WARNING! DEVICE IS 150 FEET OUTSIDE OF ZONE", providing the exact distance of the tracking device from the specified geographical area where the tracking device is permitted to roam. However, the indicated distance may be from another landmark such as the center of the specified geographical area. Additionally, the indication 750A provides the latitude and longitude of the tracking device, indicating that the tracking device is located at 30°20'13"N, 81°39'41"W. The indication 750A also provides the time that the notification was presented. Additionally, the indication 750A indicates the city, state, street and address that the tracking device is positioned in or proximate to, with the indication 750A stating that the device is located proximate to 129 Southpoint Drive, Jacksonville, Florida. However, other information such as the town, neighborhood, or zip code that the tracking device is positioned in or proximate to may be provided.

In some embodiments, one or more processors may determine whether the tracking device is positioned outside of the specified geographical area, and then an indication of the geographical location may be sent, with the indication being a notification that the tracking device is outside of the specified geographical area or a notification to the police or other authorities.

Figure 7B:
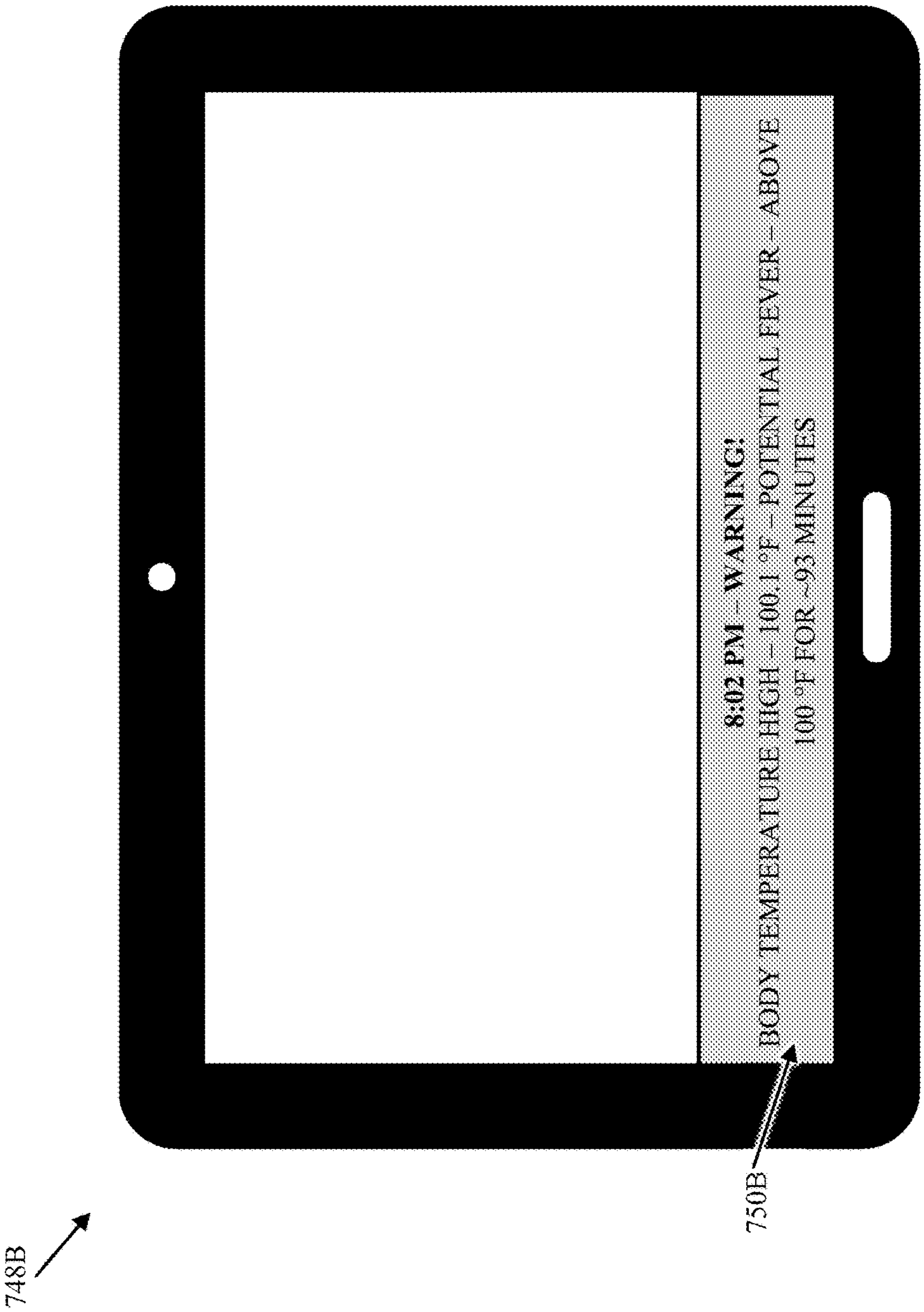
FIG. 7B is a schematic view illustrating an example of an additional device in the form of a tablet, with the additional device presenting an indication of the body temperature detected at the tracking device, in accordance with some embodiments discussed herein.

In other embodiments, processor(s) in the tracking device or elsewhere may cause an indication of the body temperature at the tracking device to be sent to the device 748B. In FIG. 7B, the device 748B is provided in the form of a tablet, with the screen of the device 748B presenting an indication 750B of the body temperature detected at the tracking device. The indication 750B may indicate that the body temperature falls outside a normal range, and the indication 750B may indicate the specific body temperature of 100.1 degrees Fahrenheit. The indication 750B may also provide notification stating a potential illness (e.g., a fever or hypothermia), the time that the notification was presented, and/or a duration of time that the body temperature of the user wearing the device has fallen outside of the normal range (e.g., outside of a range from about 98.0° F. to about 100.0° F.). However, in other embodiments, different information may be presented, additional information may be presented, or a reduced amount of information may be presented.

Figure 7C:
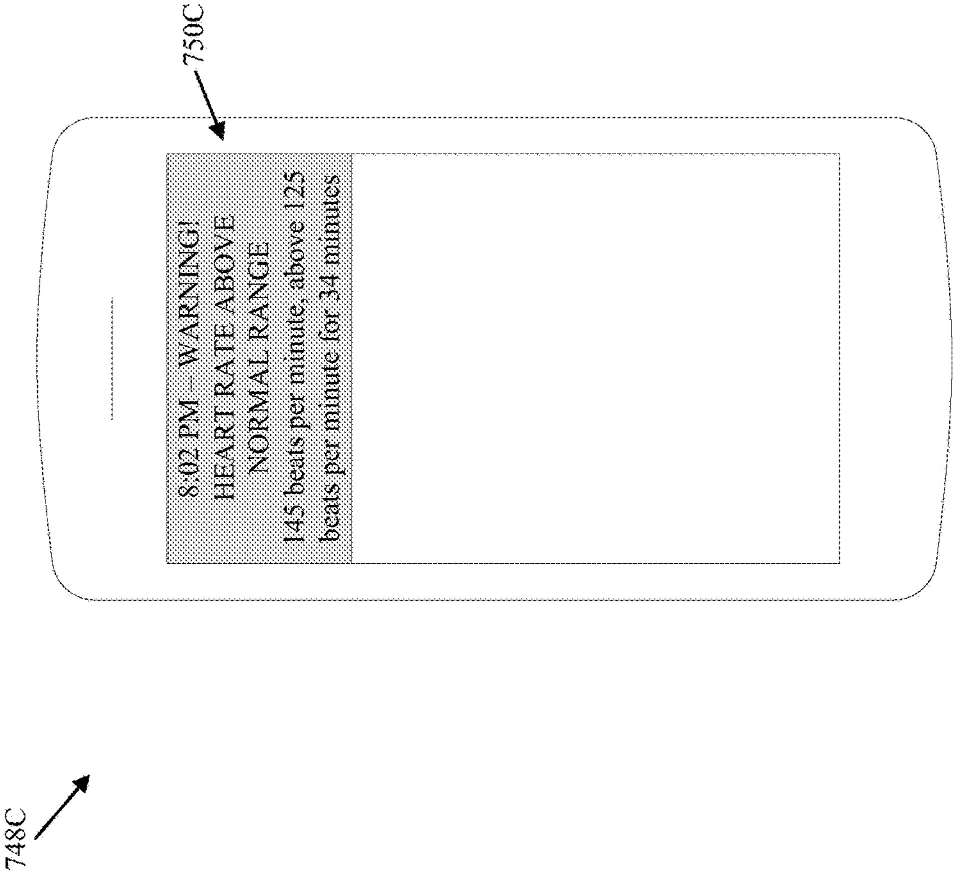
FIG. 7C is a schematic view illustrating an example of an additional device in the form of a cell phone, with the additional device presenting an alert that the heart rate of the person wearing the tracking device is above a normal range, in accordance with some embodiments discussed herein.

FIG. 7C is a schematic view illustrating an example device 748C in the form of a cell phone (e.g., a smart phone), with the device 748C presenting an indication 750C in the form of an alert. The alert states that the heart rate of the person wearing the tracking device is above a normal range. The heart rate is the non-resting heart rate, but the tracking device may be used to identify when the user has a resting heart rate falling outside of the normal range as well. In the device 748C, the alert indicates that the heart rate is above a normal range, that the heart rate is about 145 beats per minute, that the heart rate has exceeded the maximum end (e.g., about 125 beats per minute) of the normal range for about 34 minutes, and the time that the alert was presented. However, in other embodiments, different information may be presented, additional information may be presented, or a reduced amount of information may be presented.

For the example embodiments illustrated in FIGS. 7A-7C and the corresponding discussion, the indications 750A-750C may be presented as a pop-up window within the existing screen alongside other information that was previously being presented on the display. However, in other embodiments, the information that was previously being presented on the display may instead be hidden and the indications 750A-750C may spread across the entire screen of the displays. Additionally, in some embodiments, a map such as the one illustrated in FIG. 7A may replace the information previously presented on the screen. It should be understood that the various indications may be presented on any suitable electronic device and not just those illustrated in FIGS. 7A-7C.

Figure 7D:
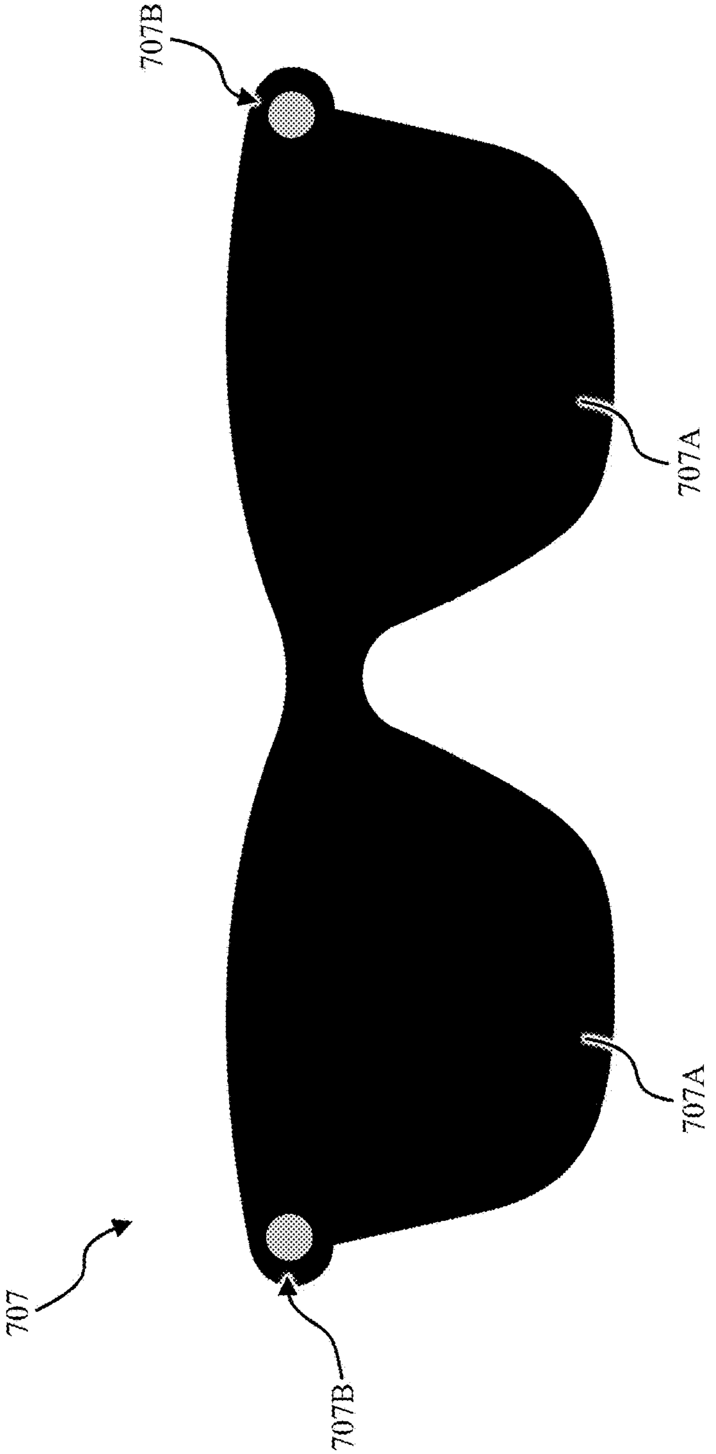
FIG. 7D is a schematic view illustrating an example of an additional device in the form of glasses having a video camera embedded therein, in accordance with some embodiments discussed herein.

FIG. 7D is a schematic view illustrating an example of an additional device in the form of glasses 707 having a video camera 707B embedded therein. The glasses 707 may be reading glasses, sunglasses, or other types of glasses. Regardless of the type, glasses 707 may be considered smart glasses in some embodiments. Glasses 707 also comprise lenses 707A and a pair of video cameras 707B. Two video cameras 707B are provided, with one video camera on each side of the glasses 707. Providing two video cameras 707B may help improve the aesthetic appearance of the glasses 707 in some embodiments, and the use of two video cameras 707B may be beneficial to provide redundancy in the event that one video camera 707B becomes inoperative for some reason. While two video cameras 707B are provided in the illustrated embodiment, a different number of video cameras 707B may be used in other embodiments. The video cameras 707B may allow video feeds to be saved in memory so that they can be retrieved by the user at a later date. Additionally, the video cameras 707B may obtain video feeds, and a substantially real-time video feeds may be presented on another device (e.g., another set of glasses 707). The video feeds may also be made available to relevant authorities, and the video feeds may be provided to other parents, loved ones, etc.

Indications may be provided on a set of glasses 707. For example, indications may be presented to the user by projecting information or images onto the lenses 707A, indications may be provided by audibly providing information to a user proximate to an ear of the user (e.g., via a speaker), indications may be provided by generating vibration of the glasses 707, or indications may be provided in other ways. In some embodiments, the glasses 707 may be paired to another set of glasses to obtain information from that other set of glasses. For example, information, images, or video feeds from one set of glasses may be transmitted to the other set of glasses 707, and the information, images, or video feeds may be presented on the lenses 707A or communicated in other ways.

The device on which the indication is provided may take various forms. In some embodiments, the device on which the indication is provided may be another similar or identical tracking device. For example, two users may wear similar tracking devices, and an alert or information may be generated and sent to a first tracking device to provide information about the second tracking device. This may be beneficial where a parent, another loved one, etc. wants to track another person to ensure his or her safety. In some embodiments, an active mode or a child safety mode may be activated to allow for active monitoring of information from a tracking device. The active mode or a child safety mode may be activated by a parent, a loved one, etc. from their own tracking device, from a computer, from a tablet, etc. In some embodiments, the parent, loved one, etc. may generate an alert independently to notify appropriate authorities of potential issues.

Figure 8A:
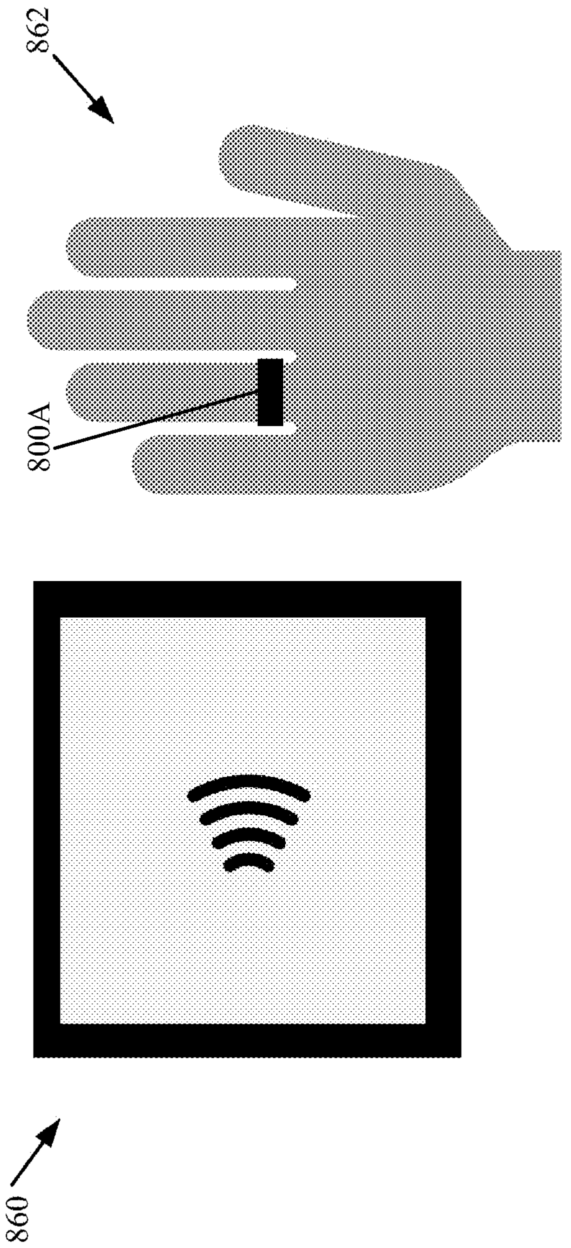
FIG. 8A is a schematic view illustrating an example tracking device in the form of a ring being used to make a wireless payment, in accordance with some embodiments discussed herein.

The tracking devices may also be used in other ways. For example, the tracking devices may be utilized to make electronic payments as illustrated in FIG. 8A. In FIG. 8A, the tracking device 800A comprises a wearable component in the form of a ring positioned on the hand 862 of the user. This tracking device 800A may be similar to the tracking device 100 of FIG. 1. Upon the tracking device 800A coming in close proximity to the payment device 860, processor(s) may cause a payment signal to be sent or received so that an electronic payment may be completed upon the payment signal being sent or received. The payment device 860 may take a variety of forms. For example, the payment device 860 may be a cellphone such as a smartphone, a tablet, a computer, or another electronic device.

Figure 8B:
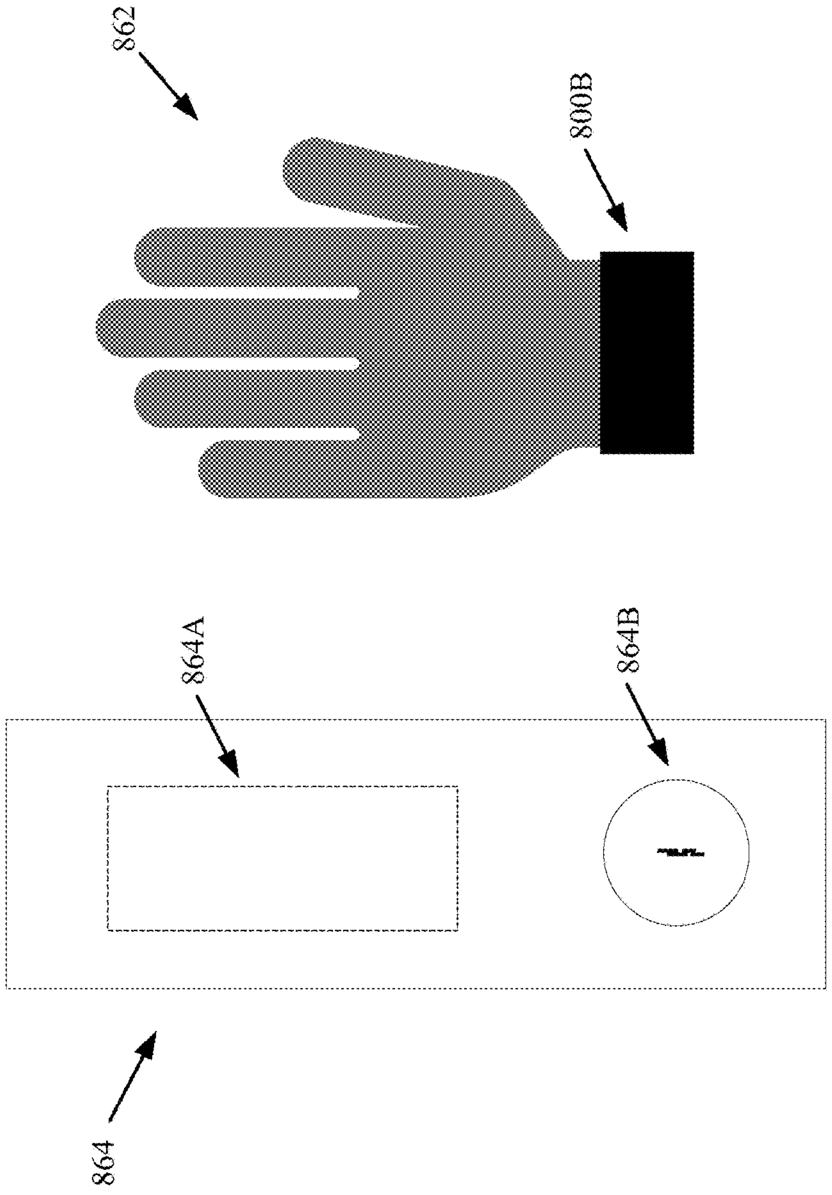
FIG. 8B is a schematic view illustrating an example tracking device in the form of a bracelet being used to unlock a lock, in accordance with some embodiments discussed herein.

Tracking devices may also be utilized to lock or unlock a door as illustrated in FIG. 8B. In FIG. 8B, the tracking device 800B comprises a wearable component in the form of a bracelet, with the bracelet being wearable on the wrist of the user and adjacent to the hand 862 of the user. Additionally, the lock 864 may comprise a mechanical lock 864B as well as an electronic lock interface 864A. Upon the tracking device 800B coming in close proximity to the electronic lock interface 864A, processor(s) may cause a lock signal to be sent or received so that the lock may be locked or unlocked upon the lock signal being received. Processor(s) may cause an actuator to lock or unlock the lock 864.

Figure 9:
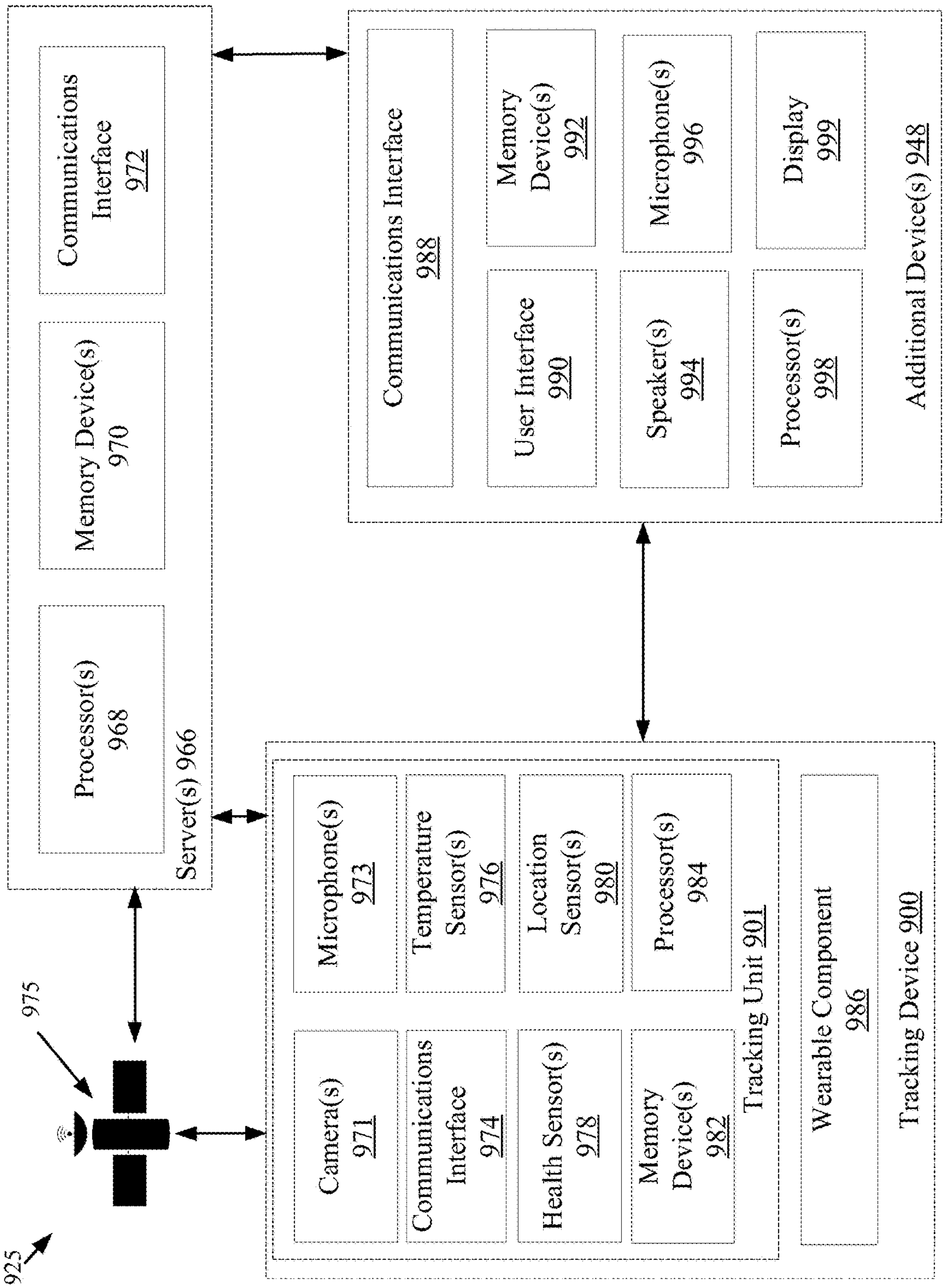
FIG. 9 is a block diagram illustrating various components of an example system for tracking a tracking device, in accordance with some embodiments discussed herein.

FIG. 9 is a block diagram illustrating various components of an example system 925 for tracking a tracking device. The system 925 comprises one or more satellites 975, one or more servers 966, one or more tracking devices 900, and one or more additional devices 948.

The server(s) 966 comprise one or more processors 968, one or more memory devices 970, and a communications interface 972. The tracking device 900 comprises wearable component 986 and a tracking unit 901. The tracking unit 901 comprises a communications interface 974, one or more temperature sensors 976, one or more health sensors 978, one or more location sensors 980, one or more memory devices 982, and one or more processors 984. Furthermore, the additional device(s) 948 comprise a communications interface 988, a user interface 990, one or more memory devices 992, one or more speakers 994, one or more microphones 996, one or more processors 998, and a display 999. The additional device 948 may be at least one of a cell phone, a pager, a display, a computer, a tablet, a server, a smart watch, another tracking device similar to those described herein, glasses, or another wearable device such as a bracelet, but the additional device 948 may be provided in other forms. The tracking device 900 may also comprise one or more camera(s) 971 and one or more microphone(s) 973 to allow the tracking device 900 to provide effective surveillance footage—where this is the case, camera(s) 971 and microphone(s) 973 may be positioned so that they are able to provide effective video and audio.

In the system 925 of FIG. 9, various connections are illustrated between components. For example, the satellite(s) 975 are illustrated as being connected to the server(s) 966 and the tracking device 900, the tracking device 900 is illustrated as being connected to the server(s) 966 and the additional device(s) 948, and the additional device(s) are illustrated as being connected to the server(s) 966 and the tracking device 900. However, the connections may be different in other embodiments. For example, one or more of the additional device(s) 948 may be connected to the satellite(s) 975. Additionally, internal connections of components within the server(s) 966, the tracking device 900, and the additional device(s) 948 are not shown, but it should be understood that these components may be connected together in a wide variety of different ways and that limited connections are illustrated to simplify FIG. 9 for the purposes of explanation.

The system 925 may include any number of different systems, modules, or components, each of which may comprise any device or means embodied in either hardware, software, or a combination of hardware and software configured to perform one or more corresponding functions described herein.

The processor(s) 968, 984, 998 may be any means configured to execute various programmed operations or instructions stored in a memory device (e.g., memory devices 970, 982, 992) such as a device or circuitry operating in accordance with software or otherwise embodied in hardware or a combination of hardware and software (e.g. a processor operating under software control or the processor embodied as an application specific integrated circuit (ASIC) or field programmable gate array (FPGA) specifically configured to perform the operations described herein, or a combination thereof) thereby configuring the device or circuitry to perform the corresponding functions of the processor(s) 968, 984, 998 as described herein. In some embodiments, one or more of the processor(s) 968, 984, 998 may be 1.2 gigahertz dual-core MediaTek, but other processors may also be utilized.

In an example embodiment, the memory devices 970, 982, 992 may include one or more non-transitory storage or memory devices such as, for example, volatile and/or non-volatile memory that may be either fixed or removable. The memory devices 970, 982, 992 may be configured to store instructions, computer program code, health data, location data, and additional data in a non-transitory computer readable medium for use, such as by the processor(s) 968, 984, 998 for enabling the components of the system 925 to carry out various functions in accordance with example embodiments of the present invention. For example, the memory devices 970, 982, 992 may be configured to buffer input data for processing by the processor(s) 968, 984, 998. Additionally or alternatively, the memory devices 970, 982, 992 could be configured to store instructions for execution by the processor(s) 968, 984, 998. The memory devices 970, 982, 992 may include computer program code that is configured to, when executed, cause processor(s) 968, 984, 998 to perform various methods described herein. The memory devices 970, 982, 992 may serve as non-transitory computer readable mediums having stored thereon software instructions that, when executed by one or more processors, cause methods described herein to be performed. In some embodiments, the memory devices 970, 982, 992 may each comprise about 512 megabytes of random-access memory (RAM) and about 5 megabytes of read-only memory (ROM), but the memory devices 970, 982, 992 may each comprise different amounts of RAM and ROM in other embodiments.

The communications interfaces 972, 974, 988 may be configured to enable communication to other components of the system 925 (e.g. via an external network). In this manner, the additional device(s) 948 may retrieve data, which may or may not be stored in memory device(s) 982, from tracking device 900 via an external network. Additionally or alternatively, other data may be transmitted or received at the communication interfaces 972, 974, 988. For example, location data may be received from the satellite(s) 975 or from location sensor(s) 980, health data may be received or sent that is from health sensor(s) 978, temperature data may be received or sent that is from the temperature sensor(s) 976, etc.

The communications interfaces 972, 974, 988 may also include one or more communications modules configured to communicate with one another in any of a number of different manners including, for example, via a network. In this regard, the communications interfaces 972, 974, 988 may include any of a number of different communication backbones or frameworks including, for example, Ethernet, global positioning system (GPS), cellular, Wi-Fi, or other suitable networks. The network may also support other data sources, including GPS. In this regard, numerous other peripheral devices may be included in the system 925. In some embodiments, some or all of the communications interfaces 972, 974, 988, may be configured to communicate using short-range wireless technologies such as Bluetooth (e.g., Bluetooth Version 4.1 or another version), Wi-Fi, NearLink, near-field communication (NFC), low power wide area networks (LPWAN), ultra-wideband (UWB), wireless local area network (WLAN) in accordance with IEEE 802.11 (b), IEEE 802.11 (g), and/or IEEE 802.11 (n) standards, and/or low-rate wireless personal access networks (LR-WPAN) pursuant to the IEEE 802.15.4 standard.

The location sensor(s) 980 may be configured to determine the current position and/or location of the tracking unit 901 and the tracking device 900. The location may be provided in the form of satellite global positioning system coordinates received from the satellite(s) 975. By tracking the location of tracking devices using satellite(s) 975, reliance on cellular towers and networks may be avoided, and location tracking may be made more reliable as the location tracking may work even in areas where limited cellular coverage is available. The location sensor(s) 980 may comprise a global-positioning system (GPS), inertial navigation system, such as machined electromagnetic sensor (MEMS), a ring laser gyroscope, or other location detection system. Alternatively or in addition to determining the location of the tracking unit 901 or the tracking device 900, the location sensor(s) 980 may also be configured to determine the direction of movement for the tracking unit 901 and/or the tracking device 900.

The display 999 (e.g. one or more screens) may be configured to present images and may include or otherwise be in communication with a user interface 990 configured to receive input from a user. The display 999 may be, for example, a conventional LCD (liquid crystal display), a touch screen display, or any other suitable display known in the art upon which images may be displayed.

In some embodiments, the display 999 may present one or more sets of data (or images generated from the one or more sets of data). Such data includes weather data, location data, position data, orientation data, health data, temperature data, or any other type of information relevant to the tracking device 900. Health data may be received from health sensor(s) 978 of the tracking unit 901 on the tracking device 900, and temperature data may be received from temperature sensor(s) 976 of the tracking unit 901 on the tracking device 900.

The user interface 990 may include, for example, a keyboard, keypad, function keys, buttons, a mouse, a scrolling device, input/output ports, a touch screen, or any other mechanism by which a user may interface with the system.

Connections between various components may be wireless connections as noted above. However, in some embodiments, the connections may be wired or direct connections. For example, data from the tracking device may be transferred to one or more additional devices 948 when the tracking device is directly connected to the additional device(s) 948 (e.g., when the tracking device is being charged). While certain devices are illustrated in the system 925 of FIG. 9, it should be understood that additional devices or components may be added to the system 925 and that some of the illustrated devices or components of system 925 may be omitted in some embodiments.

Figure 10:
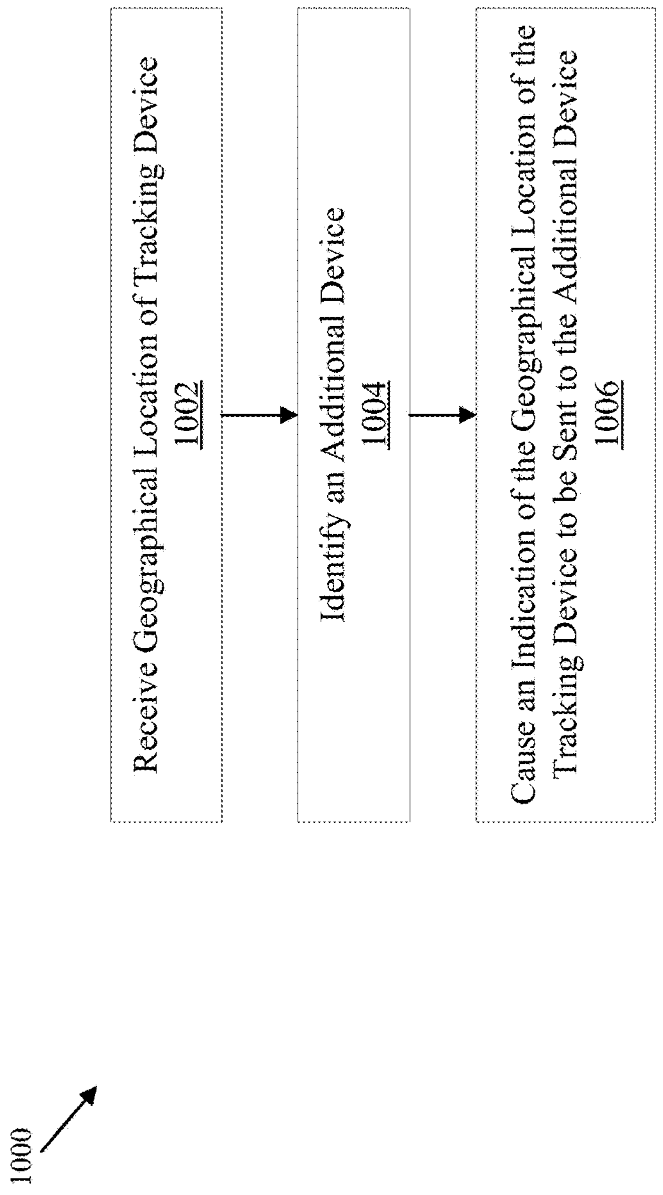
FIGS. 10-11 are flow charts illustrating example methods for tracking the location of a tracking device, in accordance with some embodiments discussed herein.

Various embodiments are also directed to methods for using tracking devices in different ways. FIG. 10 is a flow chart illustrating an example method 1000 for tracking the location of a tracking device. At operation 1002, a geographical location of the tracking device is received. At operation 1004, an additional device is identified. At operation 1006, sending of an indication of the geographical location of the tracking device to the additional device is caused. In some embodiments, method 1000 may be performed by one or more processors 984 (see FIG. 9) within a tracking unit 901 (see FIG. 9) of a tracking device 900 (see FIG. 9), but method 1000 may be performed by other processor(s) or other devices. For example, the processor(s) could be located in remote server(s) or other device(s).

Figure 11:
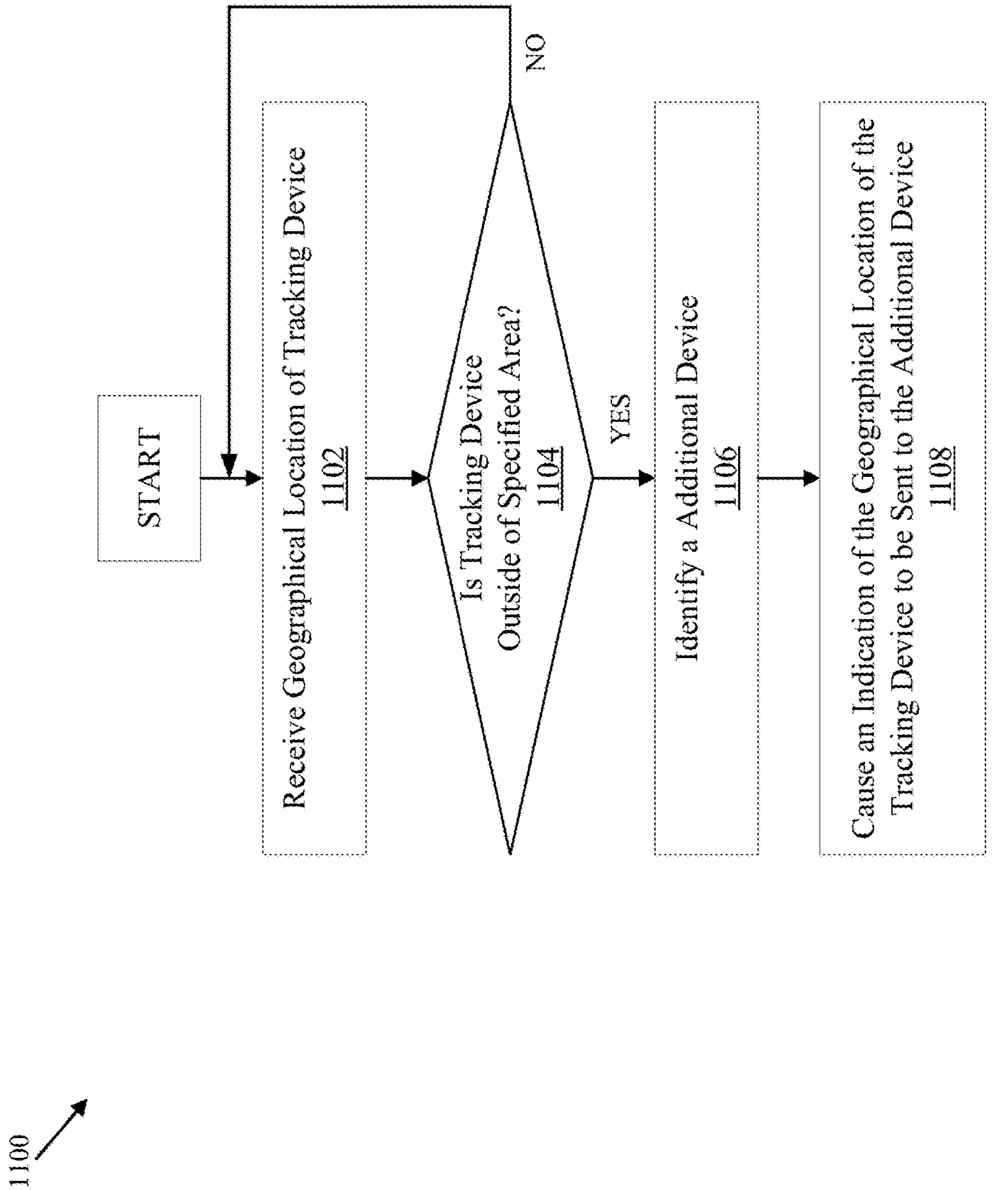

A more detailed example method 1100 for tracking the location of a tracking device is illustrated in FIG. 11. At operation 1102, a geographical location of the tracking device is received. At operation 1104, a determination is made as to whether or not the tracking device is outside of the specified area. If the tracking device is not outside of the specified area, then the method 1100 may loop back to perform operation 1102 again. If the tracking device is outside of the specified area, then the method 1100 may proceed to operation 1106. At operation 1106, an additional device is identified. At operation 1108, sending of an indication of the geographical location of the tracking device to the additional device is caused. In some embodiments, method 1100 may be performed by one or more processors 984 (see FIG. 9) within a tracking unit 901 (see FIG. 9) of a tracking device 900 (see FIG. 9), but method 1100 may be performed by other processor(s) or other devices. For example, the processor(s) could be located in remote server(s) or other device(s).

Figure 12:
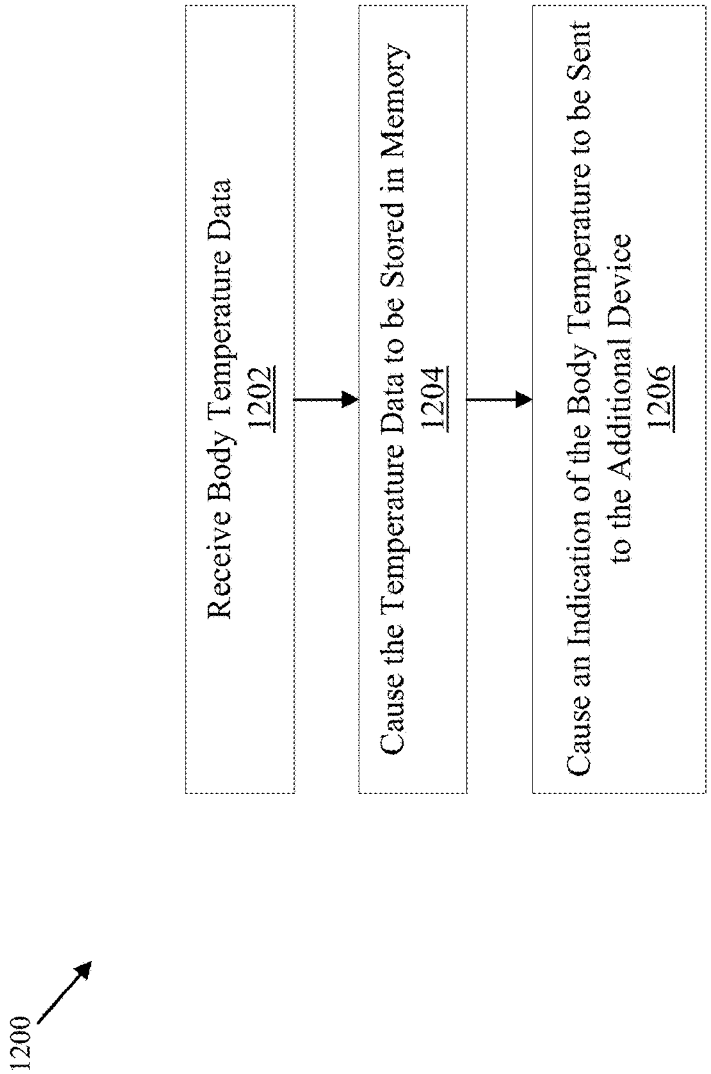
FIG. 12 is a flow chart illustrating an example method for tracking body temperature data at a tracking device, in accordance with some embodiments discussed herein.

The tracking device may also be utilized to track health information such as the temperature of the user, and FIG. 12 illustrates an example method 1200 for tracking body temperature data at a tracking device. At operation 1202, body temperature data is received. Body temperature data may be received from temperature sensor(s) 976 (see FIG. 9) or from health sensor(s) 978 (see FIG. 9). At operation 1204, storage of the temperature in memory may be caused. At operation 1206, sending of an indication of the body temperature to an additional device may be caused. In some embodiments, method 1200 may be performed by one or more processors 984 (see FIG. 9) within a tracking unit 901 (see FIG. 9) of a tracking device 900 (see FIG. 9), but method 1200 may be performed by other processor(s) or other devices. For example, the processor(s) could be located in remote server(s) or other device(s).

Figure 13:
FIG. 13 is a flow chart illustrating an example method for tracking health data at a tracking device, in accordance with some embodiments discussed herein.

Other health information may also be tracked, and FIG. 13 is a flow chart illustrating an example method 1300 for tracking health data at a tracking device. At operation 1302, health data is received. The health data may be related to a health aspect such as the heart rate, a body temperature, a blood characteristic level (e.g., glucose, oxygen, etc.), or a breathing rate. At operation 1304, storage of the health data to memory may be caused. At operation 1306, sending of the health data to the additional device may be caused. In some embodiments, method 1300 may be performed by one or more processors 984 (see FIG. 9) within a tracking unit 901 (see FIG. 9) of a tracking device 900 (see FIG. 9), but method 1300 may be performed by other processor(s) or other devices. For example, the processor(s) could be located in remote server(s) or other device(s).

Figure 14:
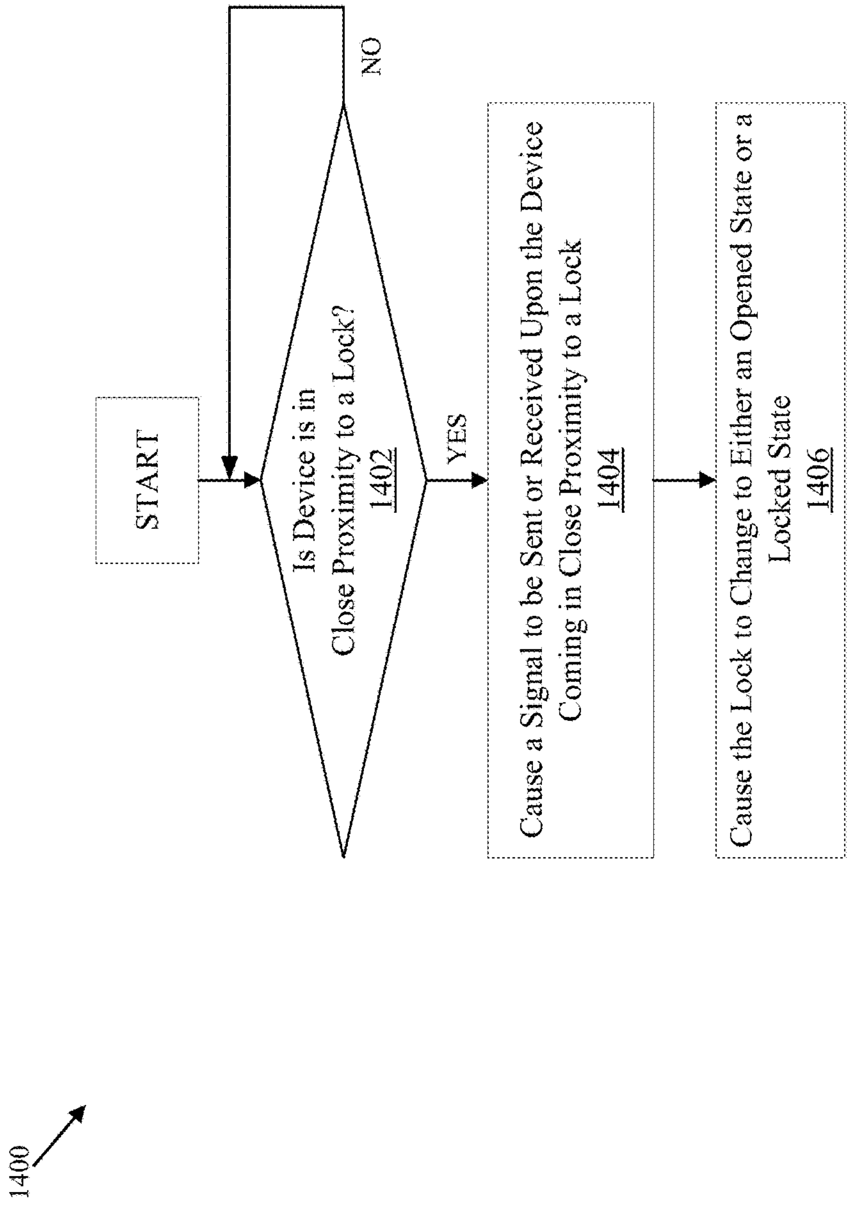
FIG. 14 is a flow chart illustrating an example method for unlocking a lock using a tracking device, in accordance with some embodiments discussed herein.

The tracking device may also be utilized to lock or unlock a lock, and FIG. 14 is a flow chart illustrating an example method 1400 for unlocking or unlocking a lock using a tracking device. At operation 1402, a determination may be made that the device is in close proximity to a lock. The determination may be made by determining whether a signal has been received indicating that the device is in close proximity such as an NFC signal, a Bluetooth signal, or another short-range wireless signal. Alternatively, a current location of the device may be matched to a location for the lock, such as using satellites or other location tracking technology. If the device is not in close proximity to the lock, then the method 1400 may remain at operation 1402 until the device comes in close proximity to the lock. If it is determined that the device is in close proximity to the lock, then the method 1400 may proceed to operation 1404. At operation 1404, sending or receiving of a signal may be caused upon the device coming in close proximity to the lock. At operation 1406, changing of the lock from an opened state to a locked state or from a locked state to an opened state may be caused. In some embodiments, method 1400 may be performed by one or more processors 984 (see FIG. 9) within a tracking unit 901 (see FIG. 9) of a tracking device 900 (see FIG. 9), but method 1400 may be performed by other processor(s) or other devices. For example, the processor(s) could be located in remote server(s) or other device(s).

Figure 15:
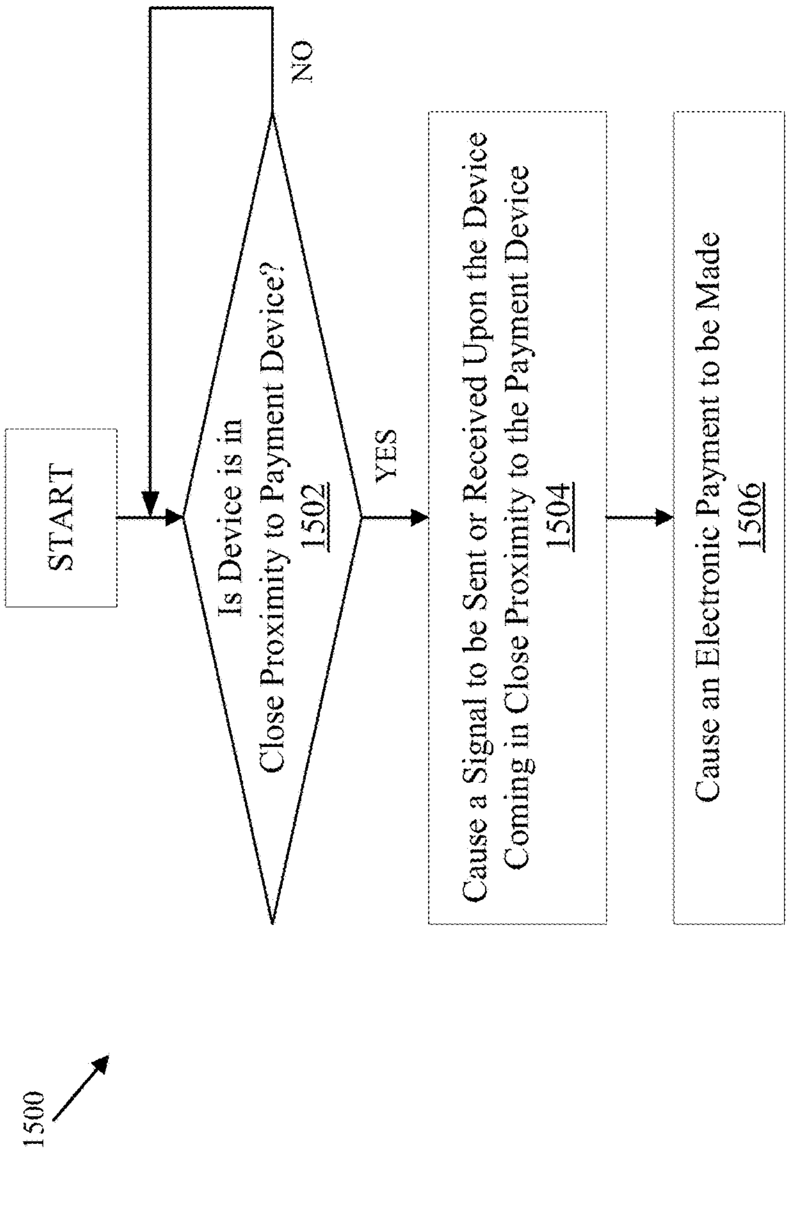
FIG. 15 is a flow chart illustrating an example method for causing an electronic payment to be made using a tracking device, in accordance with some embodiments discussed herein.

The tracking device may also be utilized to make an electronic payment, and FIG. 15 is a flow chart illustrating an example method 1500 for causing an electronic payment to be made using a tracking device. At operation 1502, a determination is made that the device is in close proximity to a payment device. The determination may be made by determining that a signal has been received indicating that the device is in close proximity such as an NFC signal, a Bluetooth signal, or another short-range wireless signal. Alternatively, a current location of the device may be matched to a location of the payment device, such as using satellites or other location tracking technology. If the device is not in close proximity to the payment device, then the method 1500 may loop back to operation 1502 until the device does come in close proximity to the payment device.

If it is determined that the device is in close proximity to the payment device, then the method 1500 may proceed to operation 1504. At operation 1504, sending or receiving of a payment signal may caused upon the device coming in close proximity to the payment device. At operation 1506, an electronic payment may be made. In some embodiments, method 1500 may be performed by one or more processors 984 (see FIG. 9) within a tracking unit 901 (see FIG. 9) of a tracking device 900 (see FIG. 9), but method 1500 may be performed by other processor(s) or other devices. For example, the processor(s) could be located in remote server (s) or other device(s).

Figure 16:
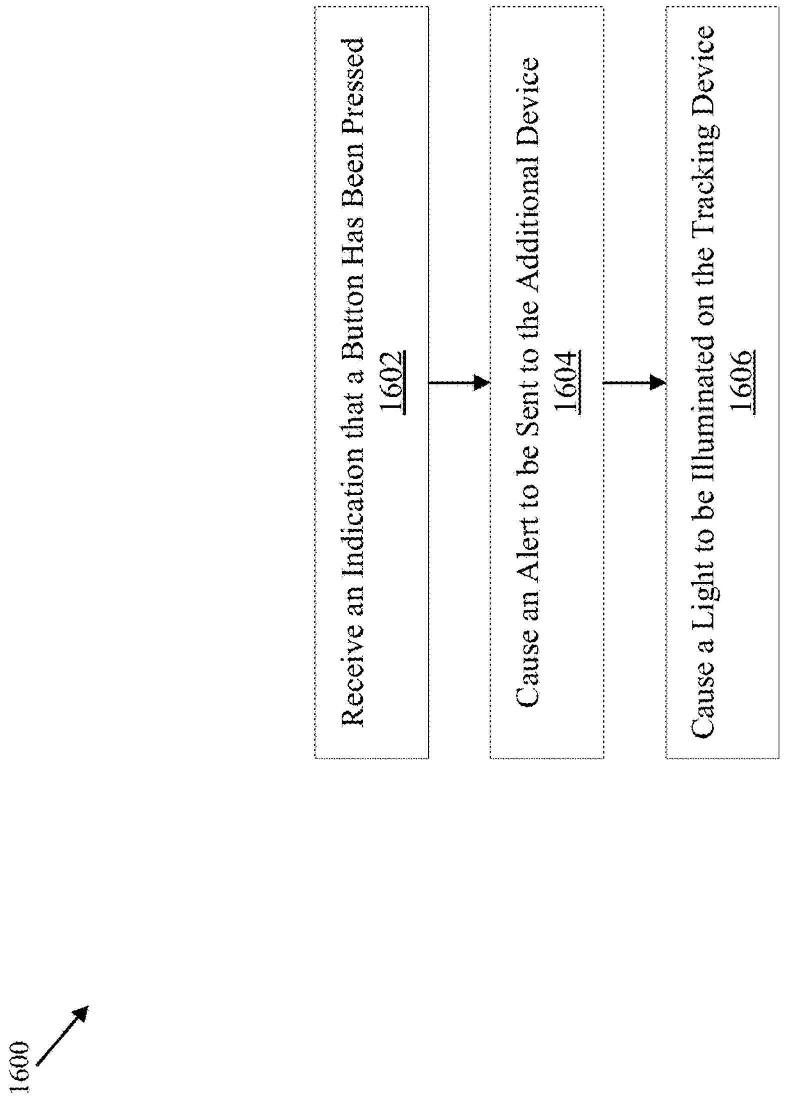
FIG. 16 is a flow chart illustrating an example method for causing an alert to be sent using a bottom of a tracking device, in accordance with some embodiments discussed herein.

The button of the tracking device may also be pressed to cause alerts to be sent to other devices and/or to cause a light on the tracking device to be illuminated. FIG. 16 is a flow chart illustrating an example method 1600 where the button is used. At operation 1602, an indication is received that a button has been pressed. At operation 1604, sending of an alert to the additional device may be caused. The additional device may be a device of government authorities such as police officers, firefighters, medical personnel, or other authorities. Alternatively, the additional device may be the device of a parent, a friend, a loved one, or another interested person. At operation 1606, a light may optionally be illuminated on the tracking device after the button has been pressed.

The various methods illustrated in FIGS. 10-16 and described above are merely exemplary, and the methods may be modified in a wide variety of different ways. For example, the methods may be combined together in some embodiments. Additionally, further operations may be added to the methods in some embodiments, or certain operations that are illustrated in the methods may be omitted. Additionally or alternatively, the operations of the methods may be rearranged into different orders or certain operations may be performed simultaneously.

CONCLUSION

Many modifications and other embodiments set forth herein will come to mind to one skilled in the art to which these embodiments pertain having the benefit of the teachings presented in the foregoing descriptions and the associated drawings. Therefore, it is to be understood that the embodiments are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

What is claimed is:

1. A system for tracking a tracking device, the tracking device comprising:

a wearable component that is at least one of a band aid, a diaper, or a pacifier, the wearable component having an attachment feature configured to enable attachment of the wearable component to at least one of a body of a person, hair, clothing, or an accessory; and a tracking unit comprising a location sensor;

an additional device;

at least one processor; and at least one memory having a computer program code stored thereon and configured to store data, the computer program code configured to, when executed by the at least one processor, cause the at least one processor to:

receive a geographical location of the tracking device based on satellite global positioning system coordinates for the location sensor;

identify the additional device;

cause an indication of the geographical location of the tracking device to be sent to the additional device; and receive health data regarding at least one health aspect of a user wearing the tracking device, the at least one health aspect being at least one of a heart rate, a body temperature, or a breathing rate; and cause the health data to be stored in the at least one memory or sent to the additional device.

2. The system of claim 1, wherein the additional device is at least one of a cell phone, a pager, a display, a computer, a tablet, or a server.

3. The system of claim 1, wherein the indication of the geographical location of the tracking device is at least one of:

a map that illustrates a position of the tracking device;

a longitude and latitude of the tracking device; or a city, town, neighborhood, or street that the tracking device is positioned in or proximate to.

4. The system of claim 1, wherein the computer program code, when executed by the at least one processor, causes the at least one processor to:

determine whether the tracking device is outside of a specified geographical area.

5. The system of claim 4, wherein the indication of the geographical location of the tracking device is a notification to police.

6. The system of claim 1, wherein the tracking device further comprises a temperature sensor configured to receive body temperature data regarding a body temperature of a user wearing the tracking device, and wherein the computer program code, when executed by the at least one processor, causes the at least one processor to:

cause an indication of the body temperature to be sent to the additional device, wherein the indication of the body temperature is at least one of a notification containing the body temperature data, a notification indicating that the body temperature of the user wearing the device falls outside of a normal range, a notification stating a potential illness, or a duration of time that the body temperature of the user wearing the device has fallen outside of the normal range.

7. The system of claim 1, wherein the computer program code, when executed by the at least one processor, causes the at least one processor to:

send or receive a signal upon the tracking device coming in close proximity to a lock; and cause a lock to be opened upon the signal being sent or received.

8. The system of claim 1, wherein at least a portion of the tracking device is waterproof.

9. The system of claim 1, wherein the at least one processor and the at least one memory are positioned in the tracking unit, and wherein the tracking unit is removably attachable to the wearable component.

10. The system of claim 1, wherein the tracking device comprises a button, wherein the computer program code, when executed by the at least one processor, causes the at least one processor to:

receive an indication that the button has been pressed; and upon receiving the indication that the button has been pressed, cause an alert to be sent to the additional device.

11. A tracking device comprising:

a wearable component that is at least one of a band aid, a diaper, or a pacifier, the wearable component having an attachment feature configured to enable attachment of the wearable component to at least one of a body of a person, hair, clothing, or an accessory; and a tracking unit comprising a location sensor, at least one processor configured to control operation of the tracking device, and at least one memory having a computer program code stored thereon and configured to store data, the computer program code configured to, when executed by the at least one processor, cause the at least one processor to:

receive a geographical location of the tracking device based on satellite global positioning system coordinates for the location sensor;

identify an additional device;

cause an indication of the geographical location of the tracking device to be sent to the additional device; and receive health data regarding at least one health aspect of a user wearing the tracking device, the at least one health aspect being at least one of a heart rate, a body temperature, or a breathing rate; and cause the health data to be stored in the at least one memory or sent to the additional device.

12. The tracking device of claim 11, wherein the additional device is at least one of a cell phone, a pager, a display, a computer, a tablet, or a server.

13. The tracking device of claim 12, wherein the indication of the geographical location of the tracking device is at least one of:

a map that illustrates a position of the tracking device;

a longitude and latitude of the tracking device; or a city, town, neighborhood, or street that the tracking device is positioned in or proximate to.

14. The tracking device of claim 13, wherein the computer program code, when executed by the at least one processor, causes the at least one processor to:

determine whether the tracking device is outside of a specified geographical area, wherein the indication of the geographical location of the tracking device is a notification that the tracking device is outside of the specified geographical area or a notification to police.

15. The tracking device of claim 11, wherein the wearable component comprises a first portion and a second portion, the at least one processor and the at least one memory being positioned in the second portion, and the second portion being removably attachable to the first portion.

16. The tracking device of claim 11, wherein the wearable component comprises a button, wherein the computer program code, when executed by the at least one processor, causes the at least one processor to:

receive an indication that the button has been pressed; and upon receiving the indication that the button has been pressed, cause an additional device to receive an alert.

17. The tracking device of claim 11, wherein the computer program code, when executed by the at least one processor, causes the at least one processor to:

send or receive a signal upon the tracking device coming in close proximity to a payment device; and cause an electronic payment to be made upon the payment signal being sent or received.

18. A system for tracking a tracking device comprising:

the tracking device comprising:

a wearable component that is at least one of a bracelet, an earring, a necklace, a ring, a band aid, a diaper, a shoe, a hat, a pacifier, a hair tie, glasses, or clothing, the wearable component having an attachment feature configured to enable attachment of the wearable component to at least one of a body of a person, hair, clothing, or an accessory; and a tracking unit comprising a location sensor;

an additional device;

at least one processor; and at least one memory having a computer program code stored thereon and configured to store data, the computer program code, when executed by the at least one processor, is configured to cause the at least one processor to:

receive a geographical location of the tracking device based on satellite global positioning system coordinates for the location sensor;

identify the additional device;

cause an indication of the geographical location of the tracking device to be sent to the additional device;

send or receive a signal upon the tracking device coming in close proximity to a payment device; and cause an electronic payment to be made upon the payment signal being sent or received.

19. The system of claim 18, wherein the wearable component is at least one of a band aid, a diaper, or a pacifier.

* * * * *